US010822429B2

(12) United States Patent
Manning et al.

(10) Patent No.: US 10,822,429 B2
(45) Date of Patent: Nov. 3, 2020

(54) ETANERCEPT FORMULATIONS EXHIBITING MARKED REDUCTION IN SUB-VISIBLE PARTICLES

(71) Applicant: Coherus Biosciences, Inc., Redwood City, CA (US)

(72) Inventors: Mark Manning, Johnstown, CO (US); Brian Murphy, Fort Collins, CO (US); Douglas Farrar, Longmont, CO (US); Alan Herman, Camarillo, CA (US)

(73) Assignee: Coherus Biosciences, Inc., Redwood City, CA (US)

( * ) Notice: Subject to any disclaimer, the term of this patent is extended or adjusted under 35 U.S.C. 154(b) by 0 days.

(21) Appl. No.: 14/592,569

(22) Filed: Jan. 8, 2015

(65) Prior Publication Data

US 2015/0125532 A1 May 7, 2015

Related U.S. Application Data

(63) Continuation of application No. PCT/US2013/049778, filed on Jul. 9, 2013.

(60) Provisional application No. 61/669,480, filed on Jul. 9, 2012, provisional application No. 61/806,235, filed on Mar. 28, 2013.

(51) Int. Cl.

| C07K 19/00 | (2006.01) |
|---|---|
| A61K 38/17 | (2006.01) |
| A61K 9/14 | (2006.01) |
| A61K 47/02 | (2006.01) |
| A61K 47/18 | (2017.01) |
| A61K 47/22 | (2006.01) |
| A61K 47/26 | (2006.01) |
| A61K 47/34 | (2017.01) |
| C07K 14/715 | (2006.01) |
| C07K 16/24 | (2006.01) |
| A61K 47/10 | (2017.01) |
| C07K 14/705 | (2006.01) |
| A61K 39/00 | (2006.01) |

(52) U.S. Cl.
CPC .............. *C07K 19/00* (2013.01); *A61K 9/14* (2013.01); *A61K 38/1793* (2013.01); *A61K 47/02* (2013.01); *A61K 47/10* (2013.01); *A61K 47/183* (2013.01); *A61K 47/22* (2013.01); *A61K 47/26* (2013.01); *A61K 47/34* (2013.01); *C07K 14/70578* (2013.01); *C07K 14/7151* (2013.01); *C07K 16/241* (2013.01); *A61K 2039/505* (2013.01); *C07K 2317/76* (2013.01); *C07K 2319/00* (2013.01); *C07K 2319/30* (2013.01)

(58) Field of Classification Search
CPC ...................................................... A61K 9/14
See application file for complete search history.

(56) References Cited

U.S. PATENT DOCUMENTS

| 5,580,856 | A | 12/1996 | Prestrelski et al. | |
|---|---|---|---|---|
| 6,171,586 | B1 | 1/2001 | Lam et al. | |
| 7,294,481 | B1 | 11/2007 | Fung | |
| 7,648,702 | B2 | 1/2010 | Gombotz et al. | |
| 7,915,225 | B2 | 3/2011 | Finck | |
| 8,758,747 | B2 | 6/2014 | Kallmeyer et al. | |
| 2003/0180287 | A1 | 9/2003 | Gombotz et al. | |
| 2006/0177444 | A1 | 8/2006 | Horizoe | |
| 2006/0292148 | A1 | 12/2006 | Matsumoto | |
| 2007/0196364 | A1 | 8/2007 | Krishnamurthy et al. | |
| 2007/0243185 | A1 | 10/2007 | Gombotz et al. | |
| 2008/0108106 | A1 | 5/2008 | Wang et al. | |
| 2008/0112953 | A1 | 5/2008 | McAuley et al. | |
| 2008/0124326 | A1* | 5/2008 | Rehder et al. | 424/133.1 |
| 2008/0213282 | A1 | 9/2008 | Jacob et al. | |
| 2008/0311119 | A1 | 12/2008 | Maloney | |
| 2009/0048122 | A1 | 2/2009 | Glaser et al. | |
| 2009/0068705 | A1 | 3/2009 | Drapeau et al. | |
| 2009/0117097 | A1 | 5/2009 | Igawa et al. | |
| 2009/0163424 | A1 | 6/2009 | Finck et al. | |
| 2009/0291062 | A1 | 11/2009 | Fraunhofer et al. | |
| 2010/0158908 | A1 | 6/2010 | Rehder et al. | |
| 2010/0166774 | A1 | 7/2010 | Dali et al. | |
| 2011/0060290 | A1 | 3/2011 | Bonk et al. | |
| 2011/0091936 | A1 | 4/2011 | Gawlitzek et al. | |
| 2011/0129468 | A1 | 6/2011 | McCue et al. | |
| 2012/0208986 | A1 | 8/2012 | Wenger et al. | |
| 2013/0150554 | A1 | 6/2013 | Melville et al. | |
| 2013/0224855 | A1 | 8/2013 | Gupta et al. | |
| 2014/0199303 | A1 | 7/2014 | Choi et al. | |
| 2014/0248274 | A1 | 9/2014 | Kallmeyer et al. | |

FOREIGN PATENT DOCUMENTS

| CN | 1244805 A | 2/2000 |
|---|---|---|
| CN | 1829739 A | 9/2006 |
| CN | 101237890 A | 8/2008 |

(Continued)

OTHER PUBLICATIONS

Translation of Examination Report for corresponding Japanese Patent Application No. 2014537220 dated Jun. 21, 2016.
Examination Report for corresponding Singaporean Patent Application No. 11201401562R dated Jan. 16, 2016.
Translation of Search Report for corresponding Taiwanese Patent Application No. 101138560 dated Jun. 27, 2016.
Translation of Examination Report for corresponding Chinese Patent Application No. 201280062761.9 dated Apr. 3, 2015.

(Continued)

*Primary Examiner* — Devang K Thakor
(74) *Attorney, Agent, or Firm* — Rothwell, Figg, Ernst & Manbeck, P.C.

(57) ABSTRACT

The invention provides stabilized aqueous pharmaceutical etanercept compositions suitable for long-term storage of etanercept, with substantial reduction in sub-visible particles, and methods of manufacture of these compositions, methods of administration, and articles of manufacture.

17 Claims, 1 Drawing Sheet

(56) References Cited

FOREIGN PATENT DOCUMENTS

| | | | |
|---|---|---|---|
| CN | 101969971 A | 2/2011 |
| CN | 102239177 A | 11/2011 |
| CN | 103930124 A | 7/2014 |
| EA | 201490195 A1 | 4/2014 |
| EA | 201391739 A1 | 5/2014 |
| EP | 1478394 A2 | 11/2004 |
| EP | 1607103 A1 | 12/2005 |
| EP | 1908482 A1 | 4/2008 |
| ES | 2311094 T3 | 2/2009 |
| JP | 2005527503 A | 9/2005 |
| JP | 2009521482 A | 6/2009 |
| JP | 2009534390 A | 9/2009 |
| JP | 2010506911 A | 3/2010 |
| JP | 2010513522 A | 4/2010 |
| JP | 2010529999 A | 9/2010 |
| JP | 2014518276 A | 7/2014 |
| JP | 2014519484 A | 8/2014 |
| JP | 2014522402 A | 9/2014 |
| TW | 200510453 A | 3/2005 |
| TW | 201311293 A1 | 3/2013 |
| WO | 1998022136 A2 | 5/1998 |
| WO | 0158473 A1 | 8/2001 |
| WO | 2003072060 A2 | 9/2003 |
| WO | 2004075918 A1 | 9/2004 |
| WO | 2005012353 A1 | 2/2005 |
| WO | 2005/037214 A2 | 4/2005 |
| WO | 2005/082377 A1 | 9/2005 |
| WO | 2005/095578 A1 | 10/2005 |
| WO | 2006/026447 A2 | 3/2006 |
| WO | 2006132363 A1 | 12/2006 |
| WO | 2007/076354 A2 | 7/2007 |
| WO | 2007076062 A2 | 7/2007 |
| WO | 2007124082 A2 | 11/2007 |
| WO | 2008045373 A2 | 4/2008 |
| WO | 2008051363 A2 | 5/2008 |
| WO | 2008079290 A2 | 7/2008 |
| WO | 2008/152075 A1 | 12/2008 |
| WO | 2008157356 A2 | 12/2008 |
| WO | 2009/111347 A1 | 9/2009 |
| WO | 2011/015926 A1 | 2/2011 |
| WO | 2011079308 A2 | 6/2011 |
| WO | 2011/134920 A1 | 11/2011 |
| WO | 2011141926 A2 | 11/2011 |
| WO | 2012/013980 A1 | 2/2012 |
| WO | 2012143418 A1 | 10/2012 |
| WO | 2012165917 A1 | 12/2012 |
| WO | 2013/006479 A2 | 1/2013 |
| WO | 2013006454 A1 | 1/2013 |

OTHER PUBLICATIONS

Translation of Examination Report for corresponding Chinese Patent Application No. 201280062761.9 dated Jan. 29, 2016.
Translation of Examination Report for corresponding Chinese Patent Application No. 201280062761.9 dated Jul. 21, 2016.
Translation of Examination Report for corresponding Eurasian Patent Application No. 201490802 dated May 14, 2015.
Translation of Examination Report for corresponding Eurasian Patent Application No. 201490802 dated Feb. 29, 2016.
Examination Report for corresponding European Patent Application No. 12841505.6 dated Jan. 28, 2015.
Translation of Examination Report for corresponding Japanese Patent Application No. 2014537221 dated Jun. 21, 2016.
Translation of Search Report for corresponding Taiwanese Patent Application No. 101138566 dated Mar. 3, 2016.
Examination Report for corresponding Australian Patent Application No. 2012326082 dated Aug. 16, 2016.
Translation of Examination Report for corresponding Chinese Patent Application No. 201280062739.4 dated Mar. 30, 2015.
International Search Report and Written Opinion for corresponding PCT application No. PCT/US2012/060738 dated Jan. 7, 2013.
Translation of Examination Report for corresponding Chinese Patent Application No. 201280062739.4 dated Jan. 29, 2016.
Translation of Examination Report for corresponding Eurasian Patent Application No. 201490803 dated Jun. 4, 2015.
Translation of Examination Report for corresponding Eurasian Patent Application No. 201490803 dated Feb. 12, 2016.
Examination Report for corresponding European Patent Application No. 12842312.6 dated Jan. 28, 2015.
Translation of Examination Report for corresponding Japanese Patent Application No. 2014537222 dated Jun. 21, 2016.
Translation of Search Report for corresponding Taiwanese Patent Application No. 101138567 dated Dec. 24, 2015.
Examination Report for corresponding Australian Patent Application No. 2012326084 dated Aug. 16, 2016.
Translation of Examination Report for corresponding Chinese Patent Application No. 201280062418.4 dated Jan. 30, 2015.
Translation of Examination Report for corresponding Chinese Patent Application No. 201280062418.4 dated Sep. 15, 2015.
Translation of Examination Report for corresponding Eurasian Patent Application No. 201490801 dated Jun. 4, 2015.
Translation of Examination Report for corresponding Eurasian Patent Application No. 201490801 dated Oct. 15, 2015.
English language translation of Examination Report for corresponding Japanese Patent Application No. 2014-537218 dated Jul. 26, 2016.
English language translation of Examination Report for corresponding Taiwanese Patent Application No. 101138560 dated Jun. 23, 2016.
Examination Report for corresponding Australian Patent Application No. 2013290289 dated Mar. 27, 2017.
English language translation of Examination Report for corresponding Bolivian Patent Application No. SP 0207-2013 dated Nov. 10, 2014.
English language translation of Examination Report for corresponding Bolivian Patent Application No. SP 0207-2013 dated Feb. 15, 2016.
English language translation of Examination Report for corresponding Chilean Patent Application Chile Nr. 0051-2015 dated Jan. 27, 2016.
English language translation of Examination Report for corresponding Eurasian Patent Application 201590161 dated Jan. 27, 2016.
English language translation of Examination Report for corresponding Japanese Patent Application 2015-521752 dated Apr. 4, 2017.
English language translation of Examination Report for corresponding Chilean Patent Application CL0572-2015 dated Aug. 22, 2016.
English language translation of Examination Report for corresponding Chinese Patent Application CN201380058650.5 dated Apr. 26, 2016.
English language translation of Examination Report for corresponding Colombian Patent Application CO15076746 dated Oct. 9, 2017.
EP Examination Report issued for EP14776207.4 dated May 27, 2016.
Tellez, CM, et al., Method for the characterization of size-exclusion chromatography media for preparative purification of DNA restriction fragments, Jun. 1999, Biotechnology Techniques, 13(6), 395-401.
Caporali R, et al., Diffuse skin reaction after changing the etanercept formulation, Nov. 1, 2008, Clinical and Experimental Rheumatology, 26(6), 1165.
Gokarn YR, et al., Excipients for protein drugs, Excipient development for pharmaceutical, biotechnology, and drug delivery systems, Jan. 1, 2006, 291-331.
Niazi, SK. "Enbrel" Handbook of pharmaceutical manufacturing formulations: Sterile products, 2009, 410.
Zimmer A, Galenische formulierung rekombinanter Wirkstoffe: problem arzneistoffstabilitat, Pharmazie in Unserer Ziet, Sep. 1, 2003, 32(5), 384-389.
Gazerani, P. et al., Effects of subcutaneous administration of glutamate on pain, sensitization and vasomotor responses in healthy men and women, Pain, Oct. 2006, 124(3), 338-348.
Bolli, R. et al., L-Proline reduces IgG dimer content and enhances the stability of intravenous immunoglobulin (IVIG) solutions, Biologicals, Jan. 2010, 38(1), 150-157.

(56) References Cited

OTHER PUBLICATIONS

EP Examination Report issued for EP15742902.8 dated Jun. 9, 2017.
Falconer R.J., et al., Stabilization of a monoclonal antibody during purification and formulation by addition of basic amino acid excipients, J Chem Technol Biotechnol, 2011, 86, 942-948.
Chari, R., et al., Long- and short-range electrostatic interactions affect the rheology of highly concentrated antibody solutions, Pharm. Res., Dec. 2009, 26(12), 2607-2618.
Chaudhri A., et al., Coarse-grained modeling of the self-association of therapeutic monoclonal antibodies, J Phys Chem B, Jul. 19, 2012, 116(28), 8045-8057.
Chaudhri A. et al., The role of amino acid sequence in the self-association of therapeutic monoclonal antibodies: insights from coarse-grained modeling, J Phys Chem B, Feb. 7, 2013, 117(5), 1269-1279.
EP Examination Report issued for EP15742902.8 dated Mar. 1, 2018.
Buck, P.M. et al., Highly viscous antibody solutions are a consequence of network formation caused by domain-domain electrostatic complementarities: insights from coarse-grained simulations, Mol Pharm, Jan. 5, 2015, 12(1), 127-139.
English language translation of Examination Report for corresponding Singapore Patent Application SG11201605860S dated May 24, 2017.
Bowers Randall et al., New Analytical Methods to Determine Calcined Coke Porosity, Shape, and Size, Light Met., vol. 2008, pp. 875-880, JSTPlus, [online], G-Search Limited., 2008, [Searched on Mar. 21, 2017], [Retrieve from: JDreamIII, internet: <URL:http://jdream3.com/>.
Heidemann, R. et al., The use of peptones as medium additives for the production of a recombinant therapeutic protein in high density perfusion cultures of mammalian cells, Cytotechnology, 2000, 32: 157-167.
Hossler, P. et al., Review: Optimal and consistent protein glycosylation in mammalian cell culture, Glycobiology, 2009, vol. 19, No. 9, pp. 936-949.
Altamirano, C. et al., Strategies for fed-batch cultivation of t-PA producing CHO cells: substitution of glucose and glutamine and rational design of culture medium, Journal of Biotechinology, 2004, 110: 171-179.
Bonarius, H. et al., Metabolic-Flux Analysis of Continuously Cultured Hybridoma Cells Using 13CO2 Mass Spectrometry in Combination with 13C-Lactate Nuclear magnetic Resonance Spectroscopy and Metabolite Balancing, Biotechnology and Bioengenieering, 2001, vol. 74, No. 6, pp. 528-538.
Reinhart D. et al., Benchmarking of commercially available CHO cell culture media for antibody production. BMC Proceedings, Dec. 4, 2013, vol. 7, No. Supp 6, pp. 13.
Examination Report for corresponding European Patent Application No. 12841765.6 dated Feb. 5, 2015.
Translation of Examination Report for corresponding Japanese Patent Application No. 2014537223 dated Jun. 21, 2016.
Examination Report for corresponding Singaporean Patent Application No. 11201401517V dated Sep. 21, 2015.
Translation of Search Report for corresponding Taiwanese Patent Application No. 101138564 dated May 26, 2016.
International Search Report and Written Opinion for corresponding PCT Application No. PCT/US2012/060739 dated Dec. 7, 2012.
International Search Report and Written Opinion for corresponding PCT Application No. PCT/US2012/060741 dated Jan. 18, 2013.
International Search Report and Written Opinion for corresponding PCT Application No. PCT/US2012/060743 dated Jan. 18, 2013.
International Search Report and Written Opinion for corresponding PCT Application No. PCT/US2012/060745 dated Jan. 18, 2013.
International Search Report and Written Opinion for corresponding PCT Application No. PCT/US2012/060748 dated Jan. 3, 2013.
Examination Report for corresponding Australian Patent Application No. 2012326168 dated Aug. 17, 2016.
Translation of Examination Report for corresponding Chinese Patent Application No. 201280062758.7 dated Jun. 30, 2015.
Translation of Examination Report for corresponding Eurasian Patent Application No. 201490815 dated Jun. 4, 2015.
Examination Report for corresponding European Patent Application No. 12842226.8 dated Jan. 28, 2015.
Translation of Examination Report for corresponding Israeli Patent Application No. 231824 dated Jun. 14, 2016.
Translation of Examination Report for corresponding Taiwanese Patent Application No. 101138561 dated Feb. 15, 2016.
Examination Report for corresponding Australian Patent Application No. 2012326170 dated Aug. 18, 2016.
Translation of Examination Report for corresponding Chinese Patent Application No. 201280062747.9 dated Jan. 27, 2015.
Translation of Examination Report for corresponding Chinese Patent Application No. 201280062747.9 dated Oct. 21, 2015.
Translation of Examination Report for corresponding Chinese Patent Application No. 201280062747.9 dated May 16, 2016.
Examination Report for corresponding European Patent Application No. 12842352.2 dated Jun. 8, 2015.
Translation of Examination Report for corresponding Japanese Patent Application No. 2014537219 dated Jul. 19, 2016.
Examination Report for corresponding Singaporean Patent Application No. 11201401563S dated Jan. 20, 2016.
Translation of Examination Report for corresponding Taiwanese Patent Application No. 101138565 dated May 24, 2016.
Examination Report for corresponding Australian Patent Application No. 2012326171 dated Aug. 22, 2016.
Translation of Examination Report for corresponding Chinese Patent Application No. 201280062748.3 dated Feb. 3, 2015.
Translation of Examination Report for corresponding Chinese Patent Application No. 201280062748.3 dated Dec. 3, 2015.
Translation of Examination Report for corresponding Eurasian Patent Application No. 201490804 dated May 25, 2015.
Translation of Examination Report for corresponding Eurasian Patent Application No. 201490804 dated Jan. 26, 2016.
Examination Report for corresponding European Patent Application No. 12841522.1 dated Jan. 28, 2015.
Wang, "Instability, stabilization, and formulation of liquid protein pharmaceuticals", International Journal of Pharmaceutics, 185 (1999), pp. 129-188.
Carpenter et al., "Overlooking Subvisible Particles in Therapeutic Protein Products: Gaps that May Compromise Product Quality", Journal of Pharmaceutical Sciences, vol. 98, No. 4, 2009, pp. 1201-1205.
Hawe et al. "Taylor Dispersion Analysis Compared to Dynamic Light Scattering for the Size Analysis of Therapeutic Peptides and Proteins and Their Aggregates", Pharm Res (2011) 28: pp. 2302-2310.
Maggio, "Use of excipients to control aggregation in peptide and protein formulations", J. Excipients and Food Chem., 1 (2) 2010, pp. 40-49.

* cited by examiner

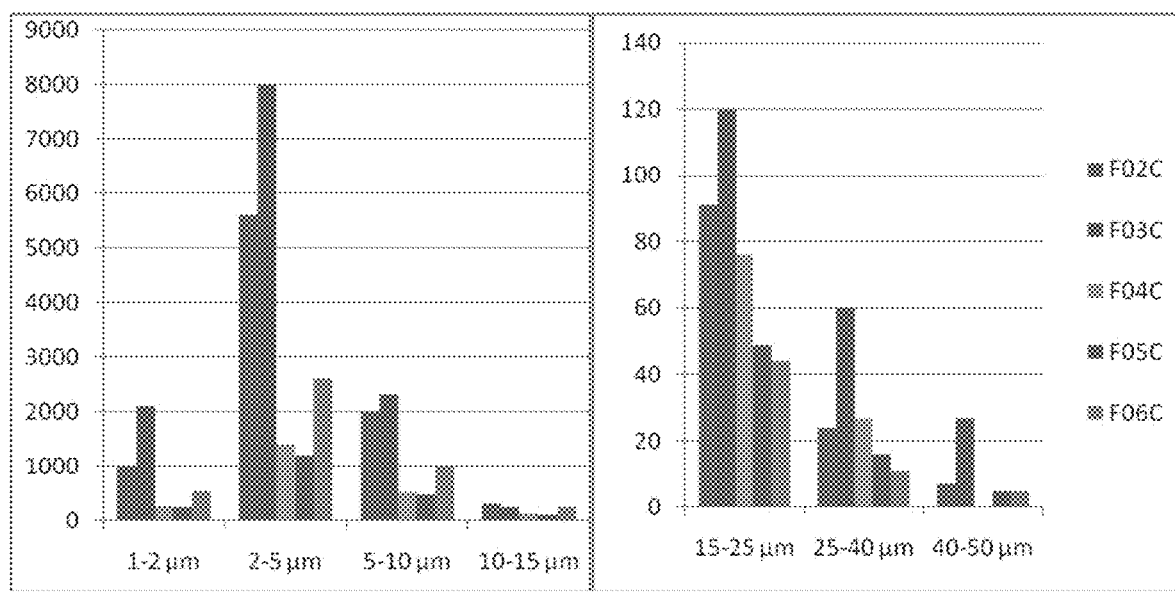

ETANERCEPT FORMULATIONS EXHIBITING MARKED REDUCTION IN SUB-VISIBLE PARTICLES

FIELD OF THE INVENTION

The present invention relates to aqueous pharmaceutical compositions stabilized for long-term storage of etanercept, methods of manufacture of the compositions, methods of their administration, and kits containing the same, wherein the stabilized etanercept compositions exhibit significant reduction in sub-visible particles. The invention includes etanercept formulations that do not require arginine for stabilization. The invention is further directed to articles and methods affording reduced patient exposure to sub-visible particles in etanercept formulations.

BACKGROUND OF THE INVENTION

Polypeptides must often be stored prior to their use. When stored for extended periods, polypeptides are frequently unstable in solution (Manning et al., 1989, Pharm. Res. 6:903-918). To extend their shelf life, additional processing steps have been developed, such as drying, e.g., lyophilization. However, lyophilized pharmaceutical compositions are less convenient to use.

Typical practices to improve polypeptide stability can be addressed by varying the concentration of elements with the formulation, or by adding excipients to modify the formulation (See, for example, U.S. Pat. Nos. 5,580,856 and 6,171,586). However, the use of additives can still result in inactive polypeptides. In addition, in the case of lyophilization, the rehydration step can result in inactivation of the polypeptide by, for example, aggregation or denaturation (Flora et al., 1992, Pharm. Res., 9:33-36; Liu et al., 1991, Biotechnol. Bioeng., 37:177-184). Aggregation of polypeptides is undesirable, as it may result in immunogenicity (Cleland et al., 1993, Crit. Rev. Therapeutic Drug Carrier Systems, 10:307-377; and Robbins et al., 1987, Diabetes, 36:838-845).

Another way to improve polypeptide stability is to use L-arginine at a specific concentration (U.S. Pat. No. 7,648,702).

One of the polypeptides that is stored for up to two years prior to use is etanercept (Enbrel®, Immunex Corporation), which is a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons (Physicians Desk Reference, 2002, Medical Economics Company Inc.) The Fc component of etanercept contains the constant heavy 2 (CH2) domain, the constant heavy 3 (CH3) domain and hinge region, but not the constant heavy 1 (CH1) domain of human IgG1. An Fc domain can contain one or all of the domains described above. Etanercept is usually produced by recombinant DNA technology in a Chinese hamster ovary (CHO) mammalian cell expression system.

A known problem in pharmaceutical protein formulations, including formulations of etanercept, is the tendency for such formulations to exhibit the presence of sub-visible particles. Such particles are believed to be associated with undesired immune reactions (immunogenicity) when protein formulations are administered to patients. Such immune reactions can reduce the effectiveness of the protein therapeutic, and may be harmful to the patient.

The present invention provides novel stable liquid formulations of etanercept that allow its long-term storage and a marked reduction in the tendency to form sub-visible particles.

SUMMARY OF THE INVENTION

The present invention provides an aqueous pharmaceutical composition comprising etanercept and a stabilizer for preventing, inhibiting or reducing the occurrence of subvisible particles in the composition, wherein the stabilizer comprises a surfactant, preferably selected from the group consisting of polysorbate surfactants and poloxamer surfactants, wherein said surfactant is capable of affording a significant reduction in sub-visible particles in the composition in comparison to an etanercept composition lacking such surfactant. The invention contemplates the use of any pharmaceutically acceptable surfactant capable of achieving the desired reduction in sub-visible particles.

In a further embodiment, the present invention is an aqueous pharmaceutical composition comprising etanercept and a stabilizer for preventing, inhibiting or reducing the occurrence of sub-visible particles in the composition, wherein the stabilizer comprises a surfactant selected from the group consisting of polysorbate surfactants and poloxamer surfactants. The stabilizer comprises a polysorbate surfactant selected from the group consisting of polysorbate 80, polysorbate 60, polysorbate 40 and polysorbate 20, or a poloxamer surfactant, such as for example Pluronic F-68. Surprisingly, the formulations of the present invention exhibit excellent stability and reduction in sub-visible particles without need for the arginine stabilizer present in commercial Enbrel® formulations. Accordingly, the formulations preferably contain no arginine, or are essentially free of arginine.

In further embodiments of the invention, the etanercept formulations containing a polysorbate or poloxamer surfactant for stabilization against sub-visible particle formation may further comprise an additional stabilizing ingredient selected from: (i) an amino acid selected from the group consisting of serine, proline and glutamate; (ii) a metal ion selected from the group consisting calcium, magnesium and zinc; (iii) a xylitol stabilizer selected from xylitol, alone, or a combination of xylitol and meglumine; (iv) a sodium chloride stabilizer selected from sodium chloride alone; sodium chloride in combination with sucrose or trehalose, and the combination of sodium chloride, sucrose and trehalose; (v) a meglumine stabilizer selected from meglumine alone; meglumine in combination with sucrose; meglumine in combination with sodium chloride; and meglumine with sodium chloride and and sucrose; and (vi) the combination of a sugar and a polyol.

Thus in one embodiment, the invention provides a stable aqueous pharmaceutical composition comprising etanercept, a polysorbate or poloxamer surfactant for stabilization against sub-visible particle formation, and a further stabilizer ingredient to inhibit instability, aggregation and/or fragmentation of the etanercept, wherein the further stabilizer comprises a compound selected from the group consisting of serine, proline and glutamate. In a preferred embodiment, the stabilizer comprises glutamate.

In another embodiment, the invention provides a stable aqueous pharmaceutical composition comprising etanercept, a polysorbate or poloxamer surfactant for stabilization against sub-visible particle formation, and a further stabilizer to inhibit instability, aggregation and/or fragmentation of the etanercept, wherein said further stabilizer comprises a stabilizing metal ion. Preferably, the surfactant is Polysorbate 80 or Pluronic F-68, and the metal ion is selected from the group consisting of calcium, magnesium, zinc, and combinations thereof. In an even more preferred embodiment, calcium, magnesium, zinc are provided as calcium chloride, magnesium chloride and zinc chloride, respectively. Calcium chloride and magnesium chloride are particularly preferred as stabilizers for etanercept.

In a further embodiment, the invention provides a stable aqueous pharmaceutical composition comprising etanercept, a polysorbate or poloxamer surfactant for stabilization against sub-visible particle formation, and a further stabilizer ingredient to inhibit instability, aggregation and/or fragmentation of the etanercept, wherein said further stabilizer is selected from the group consisting of ionic polyol derivatives, such as meglumine, mannosylglycerate, glucosylglycerate, mannosyllactate, mannosylglycolate, and diglycerolphosphate. In this embodiment, a preferred aqueous stabilized formulation of etanercept comprises: etanercept; polysorbate 80 surfactant or Pluronic F-68 surfactant; and stabilizing ingredients to retard instability, aggregation and fragmentation of the etanercept in the formulation, said stabilizing ingredients being comprised of (a) meglumine; or (b) meglumine in combination with sucrose; or (c) meglumine in combination with sodium chloride; or (d) meglumine in combination with sodium chloride and sucrose.

In yet another embodiment, the invention provides a stable aqueous pharmaceutical composition comprising etanercept, a polysorbate or poloxamer surfactant for stabilization against sub-visible particle formation, and a further stabilizer ingredient to inhibit instability, aggregation and/or fragmentation of the etanercept, wherein said further stabilizer comprises the combination of a sugar and a polyol. Preferably, surfactant is PS-80 or Pluronic F-68, the sugar is sucrose and the polyol is selected from the group consisting of mannitol and sorbitol. In a further aspect of this embodiment, the sugar is dextrose and the polyol is selected from the group consisting of mannitol and sorbitol. In a particularly preferred example of this embodiment, the invention is directed to stabilized etanercept formulation wherein a combination of sucrose and mannitol is present to provide stabilization of the etanercept monomer.

In a further embodiment, the invention provides a stable aqueous pharmaceutical composition comprising etanercept, a polysorbate or poloxamer surfactant for stabilization against sub-visible particle formation, and wherein the invention provides a further ingredient for stabilization to reduce instability, aggregation and/or fragmentation of the etanercept, said formulation comprising about 25 to about 75 mg/ml of etanercept and one or more stabilizers, wherein the further stabilizer ingredients are selected from the group consisting of (i) sodium chloride and (ii) sodium chloride in combination with sucrose or trehalose; and (iii) a combination of sodium chloride, sucrose and trehalose; and wherein the stabilizer/surfactant for reduction in sub-visible particles is preferably PS 80 or Pluronic F-68.

In yet another embodiment, the invention provides a stable aqueous pharmaceutical composition comprising etanercept, a polysorbate or poloxamer surfactant, preferably PS-80 or Pluronic F-68, for stabilization against sub-visible particle formation, and where the invention provides a further stabilizing ingredient to inhibit instability, aggregation and/or fragmentation of the etanercept, wherein the further stabilizer comprises xylitol or a combination of xylitol and meglumine.

The invention is further directed to a method for reducing the number of sub-visible particles in an etanercept formulation, said method comprising the step of adding a surfactant, preferably a polysorbate or poloxamer surfactant to an etanercept formulation in an amount constituting about 0.0001 to about 0.5 w/v % (preferably about 0.01 to 0.05 w/v %) of the formulation such that the number of subvisible particles per ml of the formulation having a size of about 1 to 10 microns is reduced by at least 50%, and preferably by at least about 60 to 70%, in comparison to the same formulation prepared in the absence of said surfactant; and where the number of sub-visible particles is measured by flowcam analysis conducted at the time the formulation is prepared and prior to any appreciable storage or thermal stress thereof.

In a further embodiment, the invention provides an article of manufacture comprising containment means containing an etanercept formulation in final dosage form, wherein the formulation comprises etanercept and a pharmaceutically acceptable surfactant, and wherein the amount of sub-visible particles present in the formulation is substantially reduced in comparison to the same formulation lacking the surfactant. The surfactant, present in the formulation in an amount in the range of 0.0005 to 1% (w/v), is preferably a polysorbate (e.g., polysorbate 80) or a polaxamer surfactant (e.g., Pluronic F-68) as referenced above. If desired, the contained formulation may include one or more of the further stabilizing ingredients discussed above. The amount of sub-visible particles in the contained formulation, determined by conventional means such as flowCAM analysis at "T0", is preferably such that the formulation has (i) less than about 2500 particles/ml having a size of about 5-10 μm; (ii) less than about 3500 particles having size of about 2-5 μm and (iii) less than about 700 particles/ml having size of about 1-2 μm. The level of sub-visible particles present in the contained etanercept/surfactant formulation preferably represents at least about a 50% to 70% reduction in sub-visible particles in comparison to the same contained formulation having no surfactant.

In yet another embodiment, the invention affords a method for reducing a subject's exposure to sub-visible particles in an etanercept formulation, said method comprising administering to the subject an etanercept formulation comprising etanercept and a pharmaceutically acceptable surfactant, and wherein the amount of sub-visible particles present in the formulation is substantially reduced in comparison to the same formulation lacking the surfactant. The surfactant, present in the formulation in an amount in the range of 0.0005 to 1% (w/v), is preferably a polysorbate (e.g., polysorbate 80) or a polaxamer surfactant (e.g., Pluronic F-68) as referenced above. If desired, the contained formulation may include one or more of the further stabilizing ingredients discussed above. The amount of sub-visible particles in the formulation, determined by conventional means such as flowCAM analysis at "T0", is preferably such that the formulation has (i) less than about 2500 particles/ml having a size of about 5-10 μm; (ii) less than about 3500 particles having size of about 2-5 μm and (iii) less than about 700 particles/ml having size of about 1-2 μm. The level of sub-visible particles present in the etanercept/surfactant formulation preferably represents at least about a 50% to 70% reduction in sub-visible particles in comparison to the same formulation having no surfactant.

Unlike commercially available etanercept, we found it surprising that each of the formulation embodiments of etanercept described and exemplified herein do not require arginine for long term stabilization, although arginine may still be added if desired. Moreover, with or without arginine, and utilizing the surfactants described herein, the formulations are able to exhibit excellent reduction in sub-visible particles. The ability to provide etanercept formulations stabilized without arginine, and exhibiting excellent resistance to subvisible particle formation, represents a potentially significant benefit to the health care system by providing patients and health care providers with alternative formulations of etanercept, including biosimilar and biobetter variants of commercial Enbrel®, that may become available at lower cost compared with present commercial etanercept formulation (i.e., Enbrel®) that require arginine for stabilization. The reduction is sub-visible particles is also seen as a very significant advantage in terms of reducing the immunogenicity of protein therapeutics.

As used herein the term "instability" or like terms denotes the tendency of the etanercept monomer to undergo a variety of undesired transformations during storage, including transformations that may result in the formation or presence of subvisible particles of varying particle size. Such transformations include the formation of very high molecular weight aggregate(s) in which multiple copies of the essentially intact etanercept monomer become randomly associated with one another through a variety of non-covalent attractions (e.g., electrostatic interactions.) Undesired transformations during storage may also include degradation of the etanercept monomer to smaller fragments and/or oligomers. Ideally, a formulaton of etanercept should minimize, to the greatest extent possible, the tendency of the formulation to result, during storage, in the formation of subvisible particles, aggregates, oligomers and/or fragments of the etanercept monomer. An important benefit resulting from the ability to reduce formation of unwanted aggregates or fragments is a reduction in the immunogenicity of the drug.

Each of the embodiments referenced above may be provided in a formulation which is optionally free, or essentially free of arginine. The term "essentially free of arginine" is intended to mean that arginine, even if present, is not contributing to the stabilization of the etanercept monomer in the formulation to such an extent that a person skilled in the art would judge its presence beneficial from a stabilization standpoint.

These and other aspects will become apparent from the following description of the various embodiments, although variations and modifications therein may be affected without departing from the spirit and scope of the novel concepts of the disclosure.

It is to be understood that both the foregoing general description and the following detailed description are exemplary and explanatory only and are not restrictive of the invention, as claimed.

BRIEF DESCRIPTION OF THE DRAWING

FIG. 1 is a bar chart representing flowCAM analysis for sub-visible particles measured at "T0" corresponding to the data in Table VIII of the specification. "T0" as explained further in the specification denotes evaluation of sub-visible particles at a point in time where the studied samples have been subject to no appreciable thermal stress or storage time. The values on the Y axis are particles per ml. In the legend: F02C is the formulation of Example 4.2 (without PS80); F03C is the formulation of Example 3.5 (without PS 80); F04C is Enbrel®; F05C is the formulation of Example 4.2 (with PS80) and F06C is the formulation of Exampe 3.5 (with PS80). The data in the graph shows a marked reduction in sub-visible particles when PS80 is present in the formulations of Examples 4.2 and 3.5, versus the same formulations containing no surfactant.

DETAILED DESCRIPTION OF THE INVENTION

Various embodiments of the invention are now described in detail. As used in the description and throughout the claims, the meaning of "a", "an", and "the" includes plural reference unless the context clearly dictates otherwise. Also, as used in the description and throughout the claims, the meaning of "in" includes "in" and "on" unless the context clearly dictates otherwise. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

"Around," "about" or "approximately" shall generally mean within 20 percent, within 10 percent, within 5, 4, 3, 2 or 1 percent of a given value or range. Numerical quantities given are approximate, meaning that the term "around," "about" or "approximately" can be inferred if not expressly stated.

The term "etanercept" or "etanercept monomer" or "monomer" is synonymous with Enbrel®. It refers to a polypeptide which is a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons. For the purposes of the present application, the term "etanercept" also encompasses etanercept with minor modifications in the amino acid structure (including deletions, additions, and/or substitutions of amino acids) which do not significantly affect the function, potency, or avidity of etanercept. The term "etanercept" encompasses all forms and formulations of Enbrel®, including but not limited to concentrated formulations, injectable ready-to-use formulations; formulations reconstituted with water, alcohol, and/or other ingredients, and others. The term etanercept is also intended to include biosimilar or biobetter variants of the etanercept used in commercial Enbrel®. For example, a biosimilar or biobetter of etanercept may have a slightly different glycosylation profile than commercial Enbrel®. In addition a biosimilar or bio better variant of the etanercept found in commercial Enbrel® may exhibit a reduction in the amount of aggregates constituting the active etanercept ingredient.

The term "monomer" as used herein is intended to mean the dimeric etanercept fusion protein referenced above.

The term "meglumine" refers to a compound with chemical formula $H_3NHCH_2(CHOH)_4CH_2OH$, also known as 1-Deoxy-1-methylaminosorbitol; N-Methyl-d-glucamine; and 1-Deoxy-1-methylamino-D-glucitol.

The terms "mannosylglycerate," "mannosyllactate," "mannosylglycolate", and "diglycerolphosphate" are well known in the art and have their commonly accepted meanings. The following references describe these compounds in some detail: Faria et al., *Carbohydrate Res.* 2008, 343: 3025-3033; Borges et al., *Extremophiles* 2002, 6: 209-216; Faria et al., *ChemBioChem* 2003, 4: 734-741; Sawangwan et al., *Biotechnol. J.* 2010, 5: 187-191; and Pais et al., *J. Mol. Biol.* 2009, 394: 237-250. The application incorporates by reference the description of these compounds contained in these references. The term "serine" refers to an amino acid whose codons are UCU, UCC, UCA, UCG, AGU, and AGC The term "proline" refers to an α-amino acid whose codons are CCU, CCC, CCA, and CCG.

The term "glutamate" refers to a carboxylate anion or salt of glutamic acid (Glu). For the purposes of this application, the term "glutamate" also encompasses glutamic acid itself.

The term "sugar" refers to monosaccharides, disaccharides, and polysaccharides. Examples of sugars include, but are not limited to, sucrose, glucose, dextrose, and others.

The term "polyol" refers to an alcohol containing multiple hydroxyl groups. Examples of polyols include, but are not limited to, mannitol, sorbitol, and others.

The term "metal ion" refers to a metal atom with a net positive or negative electric charge. For the purposes of the present application, the term "metal ion" also includes sources of metal ions, including but not limited to metal salts.

The term "long-term storage" is understood to mean that the pharmaceutical composition can be stored for three months or more, for six months or more, and preferably for one year or more. Long term storage is also understood to mean that the pharmaceutical composition is stored either as a liquid at 2-8° C., or is frozen, e.g., at −20° C., or colder. It is also contemplated that the composition can be frozen and thawed more than once.

The term "stable" or "stabilized" with respect to long-term storage is understood to mean that etanercept contained in the pharmaceutical compositions does not lose more than 20%, or more preferably 15%, or even more preferably 10%, and most preferably 5% of its activity relative to activity of the composition at the beginning of storage. Stability also denotes a reduced tendency of an etanercept formulation to exhibit sub-visible particles after long term storage.

The term "mammal" includes, but is not limited to, a human.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "composition" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses or powders.

The terms "pharmaceutical composition" and "formulation" are used interchangeably.

The term "treatment" refers to any administration or application of remedies for disease in a mammal and includes inhibiting the disease, arresting its development, relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal. The effect may be prophylactic in terms of completely or partially preventing a disorder or symptom thereof and/or may be therapeutic in terms of a partial or complete cure for a disorder and/or adverse affect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "disease" refers to any condition, infection, disorder or syndrome that requires medical intervention or for which medical intervention is desirable. Such medical intervention can include treatment, diagnosis and/or prevention.

The term "therapeutically effective amount" refers to an amount which, when administered to a living subject, achieves a desired effect on the living subject. For example, an effective amount of the polypeptide of the invention for administration to the living subject is an amount that prevents and/or treats an integrin αvβ3-mediated disease. The exact amount will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

The term "$T_1$" refers to a point in time at which an etanercept formulation has been stored for about one week at 40° C.

The term "$T_2$" refers to a point in time at which an etanercept formulation has been stored for about two weeks at 40° C.

The term "$T_4$" refers to a point in time at which an etanercept formulation has been stored for about four weeks at 40° C.

Embodiments of the Invention

When pharmaceutical compositions containing etanercept (Enbrel®), including aqueous and lyophilized formulations of etanercept are stored on a long term basis, the activity of etanercept can be lost or decreased due to instability of the etanercept monomer via aggregation and/or degradation including formation of fragments and oligomers. Moreover, the formulation may exhibit sub-visible particles over time. Thus, the present invention provides several embodiments of aqueous formulations of etanercept that allow stable long-term storage of etanercept, and reduction in sub-visible particles, so that etanercept is stable over the course of storage either in liquid or frozen states. The provided formulations include, but are not limited to formulations which do not contain arginine and do not require any extra steps such as rehydrating.

These embodiments are explained in a greater detail below.

Etanercept

All of the compositions of the present invention contemplate the use of etanercept including biosimilar or biobetter variants of the etanercept used in commercial Enbrel®. As explained in the Background section of this application, etanercept is a dimeric fusion polypeptide consisting of the extracellular ligand-binding portion of the human 75 kilodalton (p75) tumor necrosis factor receptor (TNFR) linked to the Fc portion of human IgG1. Etanercept consists of 934 amino acids. The Fc component of etanercept contains the constant heavy 2 (CH2) domain, the constant heavy 3 (CH3) domain and hinge region of human IgG1. An Fc domain can contain one or all of the domains described above.

Etanercept suitable for storage in the present pharmaceutical composition can be produced by living host cells that express etanercept, such as hybridomas in the case of antibodies, or host cells that that have been genetically engineered to produce the polypeptide in the case of fusion polypeptides or antibodies. Methods of genetically engineering cells to produce polypeptides are well known in the art. See, e.g., Ausubel et al., eds. (1990), Current Protocols in Molecular Biology (Wiley, New York). Such methods include introducing nucleic acids that encode and allow expression of the polypeptide into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5.alpha, GM2929, JM109, KW251, NM538, NM539, and any *E. coli* strain that fails to cleave foreign DNA. Fungal host cells that can be used include, but are not limited to, *Saccharomyces cerevisiae*, *Pichia pastoris* and *Aspergillus* cells. A few examples of animal cell lines that can be used are CHO, VERO, BHK, HeLa, Cos, MDCK, 293, 3T3, and W138. New animal cell lines can be established using methods well know by those skilled in the art (e.g., by transformation, viral infection, and/or selection). Optionally, etanercept can be secreted by the host cells into the medium.

Purification of the expressed etanercept can be performed by any standard method. When etanercept is produced intracellularly, the particulate debris is removed, for example, by centrifugation or ultrafiltration. When etanercept is secreted into the medium, supernatants from such expression systems can be first concentrated using standard polypeptide concentration filters. Protease inhibitors can also be added to inhibit proteolysis and antibiotics can be included to prevent the growth of microorganisms.

Etanercept can be purified using, for example, hydroxyapatite chromatography, gel electrophoresis, dialysis, and affinity chromatography, and any combination of known or yet to be discovered purification techniques, including but not limited to Protein A chromatography, fractionation on an ion-exchange column, ethanol precipitation, reverse phase HPLC, chromatography on silica, chromatography on heparin SEPHAROSET®, an anion or cation exchange resin chromatography (such as a polyaspartic acid column), chromatofocusing, SDS-PAGE, and ammonium sulfate precipitation.

I. Etanercept Stabilized with Surfactant, Plus Serine, Proline or Glutamate

In one embodiment, the invention provides a stable aqueous pharmaceutical composition comprising etanercept, a polysorbate or poloxamer surfactant, and a stabilizer to inhibit instability, aggregation and/or fragmentation of the etanercept, wherein the stabilizer comprises a compound selected from the group consisting of serine, proline and glutamate. In a preferred embodiment, the stabilizer comprises glutamate.

Without intending to be bound to any particular theory of the invention, it is believed that serine, proline and glutamate act as stabilizers to reduce etanercept's tendency to associate in undesired ternary or quaternary complexes, and therefore to reduce aggregation of etanercept. The reduction in aggregation is believed to last for a long period of time, e.g., two years or more. It is believed that serine, proline and glutamate are able to stabilize aqueous pharmaceutical compositions containing etanercept because they are excluded from the surface of the protein, resulting in net conformation stabilization. The stabilizing effects of serine, proline and/or glutamate include but are not limited to the benefits of reduced aggregation of the etanercept monomer in formulations containing the monomer.

The pharmaceutical compositions of the invention may be prepared by combining a purified etanercept and the stated stabilizers. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In a preferred embodiment, the concentration of the serine, proline or glutamate stabilizer in the provided formulations is preferably up to about 150 mM.

Serine, proline and glutamate are available from commercial suppliers.

In an embodiment in which the stabilizer comprises surfactant and glutamate, a formulation of the invention can comprise about 0.01 to about 0.05% w/v of the polysorbate or poloxamer surfactant; about 25 to about 50 mg/ml of etanercept; up to 150 mM glutamate; less than about 6 wt % sucrose; optionally up to about 100 mM NaCl; about 1 to about 30 mM sodium phosphate, and wherein the formulation has pH 6.0 to about pH 7.0 and more preferably about 6.0 to about 6.6, and most preferably between about 6.3 to about 6.5.

In an embodiment in which the stabilizer comprises surfactant and serine, a formulation of the invention can comprise about 0.01 to about 0.05% w/v of the polysorbate or poloxamer surfactant; about 25 to about 50 mg/ml of etanercept; less than about 150 mM serine; about 0.5 to about 3 wt % sucrose; about 1 to about 30 mM sodium phosphate, and wherein the formulation has pH 6.0 to about pH 7.0 and more preferably about 6.0 to about 6.6, and most preferably between about 6.3 to about 6.5.

In an embodiment in which the stabilizer comprises proline, a formulation of the invention can comprise about 0.01 to about 0.05% w/v of the polysorbate or poloxamer surfactant; about 25 to about 50 mg/ml of etanercept; less than about 150 mM proline; about 0.5 to about 3 wt % sucrose; about 1 to about 30 mM sodium phosphate, about 15 to about 100 mM NaCl; and wherein the formulation has pH 6.0 to about pH 7.0 and more preferably about 6.0 to about 6.6, and most preferably between about 6.3 to about 6.5.

Etanercept formulations according to the present invention comprising serine, proline or glutamate are preferably characterized by an SEC analysis at $T_2$ of: about 80 to about 95 wt % monomer content; less than about 4 wt % aggregate(s) content; and less than about 8 wt % fragment 3 content.

In formulations containing serine, proline or glutamate for stabilization, the formulations are more preferably characterized by:
  (a) an SEC analysis at $T_4$ of greater than about 90, 91, 92, 93, 94, 95, 96, or 97 wt % monomer content; and less than about 3, 2 or 1 wt % aggregate(s) content; and
  (b) an HIC analysis at $T_2$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than about 20, 19, 18, 17, 16, 15, 14, or 13 wt %; and
  (c) an HIC analysis at $T_4$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than 20, 19, 18, 17, 16, 15, 14 or 13 wt %.

The terms "SEC", "$T_2$" "$T_4$" "HIC" "monomer content" "aggregate(s)" and "fragment 3" "peak 1," "peak 2," and "peak 3," are defined in the examples below.

In particularly preferred formulations containing surfactant plus serine, proline or glutamate for stabilization preferably are characterized by having an HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt. %, and most preferably greater than about 99 wt %; and the amount of the composition represented by peak 3 of the HIC chromatogram is less than about 1 wt %.

A further preferred formulation using surfactant plus serine, proline and/or glutamate for stabilization of etanercept comprises about 50 mg/ml etanercept; less than about 150 mM serine, proline or glutamate, and most preferably glutamate; about 0 to 3% sucrose; about 1 to 30 mM phosphate buffer, and having a pH of about 6.0 to 6.6; and characterized by: an SEC analysis at $T_4$ of greater than about 97 wt. % monomer content and less than about 1 wt % aggregate(s) content; an HIC analysis at $T_2$ wherein the amount of the composition represented by peak 1 of the HIC chromatogram is less than about 3 wt %; the amount of the composition represented by peak 2 of the HIC chromatogram is greater than about 82 wt %; and the amount of the composition represented by peak 3 of the HIC chromatogram is less than about 15 wt %; and an HIC analysis at $T_4$ wherein the amount of the composition represented by peak 1 of the HIC chromatogram is less than about 2 wt %; the amount of the composition represented by peak 2 of the HIC chromatogram is greater than about 84 wt %; and the amount of the composition represented by peak 3 of the HIC chromatogram is less than about 13 wt %.

A further preferred glutamate stabilized etanercept formulation comprises: about 0.01 to about 0.05% w/v of the polysorbate or poloxamer surfactant; about 50 mg/ml etanercept; about 120 mM glutamate; about 1% sucrose, and about 25 mM phosphate; having a pH of about 6.3 to about 6.5, and exhibiting the SEC and HIC analytical characteristics referenced above.

Although the invention does not exclude the use of arginine, the etanercept formulations comprising about 0.01 to about 0.05% w/v of the polysorbate or poloxamer surfactant; plus serine, proline and/or glutamate for additional stabilization according to the present invention are preferably free or essentially free of arginine.

II. Etanercept Stabilized with Surfactant Plus a Metal Ion

In another embodiment, the invention provides a stabilized aqueous pharmaceutical composition comprising etanercept, about 0.01 to about 0.05% w/v of the polysorbate or poloxamer surfactant; and a stabilizer to inhibit instability, aggregation and/or fragmentation of the etanercept, wherein the stabilizer comprises a stabilizing metal ion.

It is believed that metal ions such as calcium, magnesium, and zinc reduce etanercept's tendency to associate in undesired ternary or quaternary complexes, and therefore, reduce aggregation of etanercept. The reduction in aggregation is believed to last for a long period of time, e.g., two years or more. Without wishing to be bound to a particular theory, it is believed that metal ions are able to stabilize aqueous pharmaceutical compositions containing etanercept because the metal can bind to the native state, where the right geometry of ligands occurs. In doing so, there is a net stabilization of the native state. Once the protein unfolds, the binding site is lost, and the denatured state in relatively unaffected in terms of free energy. The result is a net stabilization of the conformation, leading to improved long-term storage. In addition, metal biding may also improve the colloidal stability of the protein, elading to decreased aggregation and increased solubility. The stabilization effects of metal ion are may not be limited to reduction in aggregates but may also address other aspects of instability of the etanercept monomer in the formulation.

In a preferred embodiment, the metal ion is selected from the group consisting of calcium, magnesium, zinc, and combinations thereof. In an even more preferred embodiment, calcium, magnesium, and zinc are provided as calcium chloride, magnesium chloride and zinc chloride, respectively.

The pharmaceutical compositions of the invention may be prepared by combining, a purified etanercept, about 0.01 to about 0.05% w/v of the polysorbate or poloxamer surfactant; and a metal ion. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In a preferred embodiment, the concentration of the metal ion in the provided formulations is preferably between about 1 mM to 0.5 M, more preferably about 1 mM to about 100 mM, more preferably about 2 mM to about 20 mM, and yet more preferably about 2 to 10 mM.

Sources of metal ions are available from commercial suppliers.

In an embodiment using surfactant plus calcium chloride for stabilization, an etanercept formulation of the invention comprises about 0.01 to about 0.05% w/v of the polysorbate or poloxamer surfactant; about 25 to about 50 mg/ml of etanercept; up to about 5 mM calcium chloride; optionally about 0.5 to 6 wt % sucrose or trehalose; optionally about 0 to 100 mM NaCl; optionally up to about 10 mM xylitol; about 1 to about 30 mM sodium phosphate; wherein the composition has a pH of about 6.0 to about pH 7.0, and more preferably about 6.0 to about 6.6 and most preferably about 6.3 to about 6.5.

In an embodiment using magnesium chloride for stabilization, an etanercept formulation of the invention comprises about 0.01 to about 0.05% w/v of the polysorbate or poloxamer surfactant; about 25 to about 50 mg/ml of etanercept; about 1 mM to about 20 mM magnesium chloride; optionally up to about 6 wt % sucrose; about 25 to 150 mM NaCl; about 1 to about 30 mM sodium phosphate; wherein the composition has a pH of about 6.0 to about pH 7.0, and more preferably about 6.0 to about 6.6 and most preferably about 6.3 to about 6.5.

Compositions stabilized with metal ions are preferably characterized as having an SEC analysis at $T_2$ of: about 80 wt % to about 95 wt % monomer content; an SEC analysis at $T_2$ of aggregate(s) content of less than about 4 wt %; and an SEC analysis at $T_2$ of fragment 3 content of less than about 8 wt %.

More preferably the etanercept formulations containing a stabilizing metal ion according to the invention are characterized by:

(a) an SEC analysis at $T_4$ of greater than about 90, 91, 92, 93, 94, 95, 96, or 97 wt % monomer content; and less than about 3, 2 or 1 wt % aggregate(s) content; and (b) an HIC analysis at $T_2$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than about 20, 19, 18, 17, 16, 15, 14, or 13 wt %; and (c) an HIC analysis at $T_4$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than 20, 19, 18, 17, 16, 15, 14 or 13 wt %.

The etanercept formulations of the present invention containing surfactant plus metal ion for stabilization are more preferably characterized by having an HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt % and most preferably greater than about 99 wt %; and the amount of the composition represented by peak 3 of the HIC chromatogram is less than about 1 wt %.

The terms "SEC", "$T_2$," "$T_4$," "HIC" "monomer content" "aggregate(s)" and "fragment 3" "peak 1," "peak 2," and "peak 3," are defined in the examples below.

Preferred etanercept formulations stabilized with surfactant plus calcium chloride comprise: about 0.01 to about 0.05% w/v of the polysorbate or poloxamer surfactant; about 50 mg/ml etanercept; 1 to 5 mM calcium chloride; about 1 to 30 mM sodium phosphate; about 0 to 100 mM NaCl; about 0.5 to 5% sucrose or trehalose or combination thereof; and wherein the composition has a pH of about 6.0 to 6.6 and characterized by: an SEC analysis at $T_4$ of greater than about 97 wt. % monomer content and less than about 1 wt % aggregate(s) content; an HIC analysis at $T_2$ wherein the amount of the composition represented by peak 1 of the HIC chromatogram is less than about 4 wt %; the amount of the composition represented by peak 2 of the HIC chromatogram is greater than about 82 wt %; and the amount of the composition represented by peak 3 of the HIC chromatogram is less than about 15 wt %; and an HIC analysis at $T_4$ wherein the amount of the composition represented by peak 1 of the HIC chromatogram is less than about 2 wt %; the amount of the composition represented by peak 2 of the HIC chromatogram is greater than about 85 wt %; and the amount of the composition represented by peak 3 of the HIC chromatogram is less than about 13 wt %.

Preferred etanercept formulations stabilized with surfactant plus magnesium chloride comprise: about 0.01 to about 0.05% w/v of the polysorbate or poloxamer surfactant; about 1 mM to about 20 mM magnesium chloride; optionally up to about 6 wt % sucrose; about 25 to 150 mM NaCl; about 1 to about 30 mM sodium phosphate; wherein the composition has a pH of about 6.0 to 6.6; and wherein the composition is characterized by: an SEC analysis at $T_4$ of greater than about 97 wt. % monomer content and less than about 1 wt % aggregate(s) content; an HIC analysis at $T_2$ wherein the amount of the composition represented by peak 1 of the HIC chromatogram is less than about 4 wt %; the amount of the composition represented by peak 2 of the HIC chromatogram is greater than about 85 wt %; and the amount of the composition represented by peak 3 of the HIC chromatogram is less than about 14 wt %; and an HIC analysis at $T_4$ wherein the amount of the composition represented by peak 1 of the HIC chromatogram is less than about 2 wt %; the amount of the composition represented by peak 2 of the HIC chromatogram is greater than about 85 wt %; and the amount of the composition represented by peak 3 of the HIC chromatogram is less than about 14 wt %.

In particularly preferred embodiments of the invention using surfactant plus calcium chloride for stabilization, a stabilized etanercept formulation having the analytical properties referenced above comprises: about 50 mg/ml of etanercept; about 2 mM calcium chloride; about 15 mM sodium phosphate; about 75 mM sodium chloride; and about 3 wt % sucrose; wherein the formulation has a pH of about 6.3 to 6.5.

In a further preferred embodiment of the invention using surfactant plus magnesium chloride for stabilization, a stabilized etanercept formulation having the analytical properties referenced above comprises: about 0.01 to about 0.05% w/v of the polysorbate or poloxamer surfactant; about 50 mg/ml of etanercept; about 10 mM magnesium chloride; about 15 mM sodium phosphate; about 75 mM sodium chloride; and about 3 wt % sucrose; and having a pH of about 6.3 to 6.5.

The terms "SEC", "$T_2$" "$T_4$" "HIC" "monomer content" "aggregate(s)" and "fragment 3" "peak 1," "peak 2," and "peak 3," are defined in the examples below.

Although the use of surfactant plus stabilizing metal ions according to the invention does not exclude the use of arginine, the etanercept formulations comprising metal ion for stabilization according to the present invention are preferably free or essentially free of arginine.

III. Etanercept Stabilized with Surfactant Plus an Ionic Polyol Derivative Excipient In another embodiment, the invention provides a stable aqueous formulation comprising etanercept, about 0.01 to about 0.05% w/v of the polysorbate or poloxamer surfactant; and an ionic polyol derivative excipient, wherein said excipient is selected from the group consisting of meglumine (N-methyl-D-glucamine), mannosylglycerate, glucosylglycerate, mannosyllactate, mannosylglycolate, and diglycerolphosphate.

Preferably, in this embodiment or aspect, the invention is an aqueous stabilized formulation of etanercept comprising: etanercept; about 0.01 to about 0.05% w/v of the polysorbate or poloxamer surfactant; and stabilizing ingredients to retard instability, aggregation and fragmentation of the etanercept in the formulation, said stabilizing ingredients being comprised of (a) meglumine; or (b) meglumine in combination with sucrose; or (c) meglumine in combination with sodium chloride; or (d) meglumine in combination with sodium chloride and sucrose.

Meglumine is commonly used as a small molecule excipient. We have now surprisingly found that meglumine is also able to stabilize aqueous pharmaceutical compositions containing a large protein, such as etanercept.

It is believed that meglumine reduces etanercept's tendency to associate in undesired ternary or quaternary complexes, and therefore, reduces aggregation of etanercept. The reduction in aggregation is believed to last for a long period of time, e.g., two years or more. Without wishing to be bound to a particular theory, it is believed that meglumine is able to stabilize aqueous pharmaceutical compositions containing etanercept by a combination of three different mechanisms. First, meglumine can act as an excluded solute in the same way mannitol, sucrose, and sorbitol increase conformational stability. Second, charged solutes can alter the colloidal stability, thereby reducing the propensity to self-associate, thereby slowing aggregation. Third, these ionic polyol derivatives, being charged near neutral pH, can act as salting-in agents, as arginine does, potentially resolubilizing aggregates. The stabilizing effects of meglumine are not limited to reduction in aggregates but may involve other aspects of stabilization of the etanercept monomer in a formulation containing the monomer.

The pharmaceutical compositions of the invention may be prepared by combining, a purified etanercept, about 0.01 to about 0.05% w/v of the polysorbate or poloxamer surfactant, and the ionic polyol derivative, preferably meglumine. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In a preferred embodiment, the concentration of meglumine in the provided formulations is preferably between about 0.1% (w/v) to 40% (w/v), more preferably about 1% to about 20%, more preferably about 2% to about 10%, even more preferably about 2% to about 5%.

Meglumine is available from commercial suppliers.

A preferred embodiment comprises about 25 to about 75 mg/ml etanercept, about 0.01 to about 0.05% w/v of the polysorbate or poloxamer surfactant; about 1-30 mM of sodium phosphate; up to about 10% meglumine; optionally up to about 5 wt % sucrose; and optionally up to about 100 mM sodium chloride, wherein the composition has a pH of about 6.0 to 7.0, and preferably about 6.0 to about 6.6 and most preferably about 6.3 to about 6.5.

A surfactant/meglumine stabilized etanercept composition is preferably characterized by SEC analysis at $T_2$ in which: the monomer content is greater than about 85 wt. %; aggregate(s) content is less than about 3 wt %; and fragment 3 content is less than about 8 wt. %.

A more preferred formulation of etanercept wherein an ionic polyol derivative such as meglumine is present for stabilization is one that is characterized by:
 (a) an SEC analysis at $T_4$ of greater than about 90, 91, 92, 93, 94, 95, 96, or 97 wt % monomer content; and less than about 3, 2 or 1 wt % aggregate(s) content; and
 (b) an HIC analysis at $T_2$ wherein the amount of the composition represented by peak 1 of the HIC chromatogram is less than about 4, 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than about 20, 19, 18, 17, 16, 15, 14, or 13 wt %; and
 (c) an HIC analysis at $T_4$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than 20, 19, 18, 17, 16, 15, 14 or 13 wt %.

A particularly preferred etanercept formulation stabilized with surfactant plus meglumine is characterized by HIC analysis at $T_4$ or $T_2$ wherein the amount of the composition represented by peak 1 of the HIC chromatogram is less than about 1%; the amount of the composition represented by peak 2 of the HIC chromatogram is greater than about 99 wt %; and the amount of the composition represented by peak 3 of the HIC chromatogram is less than about 1 wt %.

The terms "SEC", "$T_2$" "$T_4$" "HIC" "monomer content" "aggregate(s)" and "fragment 3" "peak 1," "peak 2," and "peak 3," are defined in the examples below.

In other embodiments meglumine can be replaced with another ionic polyol derivative of sorbitol, glycerol or mannitol, such as mannosylglycerate, glucosylglycerate, mannosyllactate, mannosylglycolate, and diglycerolphosphate (at about 0.1% to about 40%) in the formulation.

A preferred meglumine-stabilized etanercept formulation containing about 0.01 to about 0.05% w/v of the polysorbate or poloxamer surfactant, and free of arginine and exhibiting analytical properties as described above comprises about 25 to about 75 mg/ml etanercept; about 0.5 wt. % meglumine; about 25 mM phosphate; about 1% sucrose; and about 100 mM sodium chloride.

A further preferred surfactant/meglumine-stabilized etanercept formulation free of arginine and exhibiting analytical properties as described above comprises about 0.01 to about 0.05% w/v of the polysorbate or poloxamer surfactant; about 50 mg/ml etanercept; about 5 wt. % meglumine; about 25 mM phosphate.

Although the invention does not exclude the use of arginine, the etanercept formulations comprising ionic polyol derivatives such as meglumine for stabilization according to the present invention are preferably free or essentially free of arginine.

IV. Etanercept Stabilized with Surfactant and a Combination of a Sugar and a Polyol In yet another embodiment, the invention provides a stable aqueous formulation comprising etanercept, about 0.01 to about 0.05% w/v of the polysorbate or poloxamer surfactant; a sugar and a polyol.

It is believed that a combination of a sugar and a polyol reduces etanercept's tendency to associate in undesired ternary or quaternary complexes, and therefore, reduces aggregation of etanercept. The reduction in aggregation is believed to last for a long period of time, e.g., two years or more. Thus, a combination of a sugar and a polyol is believed to be able to stabilize pharmaceutical aqueous compositions containing etanercept. Without wishing to be bound to a particular theory, the combination of a sugar and a polyol is believed to be synergistic for the purposes of stabilizing etanercept because even though excluded solutes are, on average, residing in the bulk, rather than on the surface of the protein, the fact is that there will be interactions between sugars/polyols and the protein. Those interactions will likely differ between sugars and smaller polyols. In addition, at high concentrations, the two additives will alter the thermodynamic activity of the other, thereby leading to solution behavior that will be different than what would be observed for each individual component. As discussed further below, amines can be substituted for the polyol.

The pharmaceutical compositions of the invention may be prepared by combining, a purified etanercept, about 0.01 to about 0.05% w/v of the polysorbate or poloxamer surfactant; a sugar, and a polyol. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In some embodiments, a sugar and a polyol may act in concert, in the same way two metals form an alloy with properties not exhibited by either metal. It should be understood that the same approach would lead one to use amino acids, such as proline, serine, or glutamate along with a sugar to achieve a stability profile better than either excipient could provide on its own. A preferred ratio of a sugar to a polyol (or amino acid) in the alloy is believed to be between 5:1 to 1:5.

The most preferred sugars are believed to be sucrose, trehalose, lactose, raffinose, and maltose.

The most preferred polyols are believed to be sorbitol, mannitol, glycerol, and propylene glycol.

The preferred amino acids are believed to be proline, serine, threonine, and glutamate.

In a preferred embodiment, the concentration of a sugar in the provided formulations is preferably between about 0.1% (w/v) to 40%, more preferably about 1% to about 20%, more preferably about 2% to about 10%, and yet more preferably about 5% to 9%.

In a preferred embodiment, the concentration of a polyol in the provided formulations is preferably between about 0.1% to 30%, more preferably about 1% to about 10%, and yet more preferably about 2% to about 5%.

Sugars and polyols are available from commercial suppliers.

In one embodiment, a formulation of the invention comprises about 25 to about 75 mg/ml of etanercept; about 0.01 to about 0.05% w/v of the polysorbate or poloxamer surfactant; about 1% to about 10% sucrose; about 1% to about 5% mannitol; about 10 mM to about 50 mM sodium phosphate; and about 0 mM to about 100 mM NaCl, at about pH 6.3 to about pH 7.0.

In another embodiment, sucrose can be replaced with another sugar such as trehalose (at about 1% to about 10%) in the formulation. In yet another embodiment, mannitol can be replaced with another polyol such as sorbitol (at about 1% to about 5%) in the formulation.

Although the invention does not exclude the use of arginine the etanercept formulations comprising sugar and polyol (or amino acid) for stabilization are preferably free or essentially free of arginine.

V. Etanercept Stabilized with Surfactant Plus Xylitol

In yet another embodiment, the invention provides a stabilized aqueous pharmaceutical composition comprising etanercept, about 0.01 to about 0.05% w/v of the polysorbate or poloxamer surfactant; and a stabilizer to inhibit instability, aggregation and/or fragmentation of the etanercept, wherein the stabilizer comprises xylitol or a combination of xylitol and meglumine.

Without wishing to be bound to any particular theory, It is believed that xylitol reduces etanercept's tendency to associate in undesired ternary or quaternary complexes, and therefore, reduces aggregation of etanercept. The reduction in aggregation is believed to last for a long period of time, e.g., two years or more. The stabilizing effects of xylitol are not limited to reduction in aggregates but may involve other aspects of stabilization of the etanercept monomer in a formulation containing the monomer.

A preferred stabilized etanercept formulation incorporating xylitol for stabilization is one in which stabilization is provided by about 0.01 to about 0.05% w/v of the polysorbate or poloxamer surfactant; plus a combination of xylitol and meglumine.

The pharmaceutical compositions of the invention may be prepared by combining, a purified etanercept, about 0.01 to about 0.05% w/v of the polysorbate or poloxamer surfactant; and xylitol, or xylitol in combination with meglumine. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

Xylitol stabilized etanercept formulations of the invention can comprise about 25 to 75 mg/ml of etanercept; about 0.01 to about 0.05% w/v of the polysorbate or poloxamer surfactant; about 1-10 wt. % xylitol; about 1 to 30 mM sodium phosphate; optionally up to about 5 wt % meglumine; optionally up to about 5 mM NaCl; and optionally up to about 5 wt % sucrose.

Surfactant/Xylitol stabilized etanercept formulations which additionally contain meglumine, sodium chloride and sucrose can comprise, in addition to xylitol, comprise about 1-3 mM NaCl; about 1 to 5 wt % sucrose; and meglumine in an amount of about 1-5 wt. % of the composition.

In a further embodiment, xylitol stabilized etanercept formulations can comprise about 25 to about 75 mg/ml of etanercept; about 0.01 to about 0.05% w/v of the polysorbate or poloxamer surfactant; and a stabilizer to inhibit instability, aggregation and/or fragmentation of the etanercept, wherein the stabilizer is xylitol in an amount constituting up to about 10 wt. % of the composition, and wherein the composition is characterized by an SEC analysis at $T_2$ of: about 80 wt % to about 95 wt % monomer content; an SEC analysis at $T_2$ of aggregate(s) content of less than about 4 wt % and preferably less than about 3 wt %; and an SEC analysis at $T_2$ of fragment 3 content of less than about 8 wt % and preferably less than about 6 wt %; wherein the composition has a pH of about 6.0 to about pH 7.0, and more preferably about 6.0 to about 6.6 and most preferably about 6.3 to about 6.5.

In stabilized etanercept formulations such as those referenced above containing surfactant plus xylitol or surfactant plus xylitol in combination with meglumine, the formulations are more preferably characterized by:
  (a) an SEC analysis at $T_4$ of greater than about 90, 91, 92, 93, 94, 95, 96, or 97 wt % monomer content; and less than about 3, 2 or 1 wt % aggregate(s) content; and
  (b) an HIC analysis at $T_2$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than about 20, 19, 18, 17, 16, 15, 14, or 13 wt %; and
  (c) an HIC analysis at $T_4$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than 20, 19, 18, 17, 16, 15, 14 or 13 wt %.

The terms "SEC", "$T_2$," "$T_4$" "HIC" "monomer content" "aggregate(s)" and "fragment 3" "peak 1," "peak 2," and "peak 3," are defined in the examples below.

Particularly preferred formulations containing about 0.01 to about 0.05% w/v of the polysorbate or poloxamer surfactant; pus xylitol, or xylitol in combination with meglumine, are characterized by having an HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt. % and preferably greater than about 99 wt %; and the amount of the composition represented by peak 3 of the HIC chromatogram is less than about 1 wt %. Specific xylitol-stabilized formulations are provided in the detailed examples.

Although the invention does not exclude the use of arginine, the etanercept formulations comprising surfactant plus xylitol for stabilization according to the present invention are free or essentially free of arginine.

VI. Etanercept Formulations Stabilized with Surfactant Plus NaCl

In yet another embodiment, the invention provides an aqueous etanercept formulation stabilized to reduce instability, aggregation and/or fragmentation of the etanercept, said formulation comprising about 25 to about 75 mg/ml of etanercept about 0.01 to about 0.05% w/v of the polysorbate or poloxamer surfactant; and one or more stabilizers, wherein the stabilizers are selected from the group consisting of (i) sodium chloride and (ii) sodium chloride in combination with sucrose or trehalose; and (iii) a combination of sodium chloride, sucrose and trehalose.

The pharmaceutical compositions of the invention may be prepared by combining, a purified etanercept, about 0.01 to about 0.05% w/v of the polysorbate or poloxamer surfactant; and sodium chloride, optionally with sucrose and/or trehalose. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In an embodiment using surfactant plus sodium chloride for stabilization, an etanercept formulation of the invention comprises about 25 to 75 mg/ml etanercept, about 0.01 to about 0.05% w/v of the polysorbate or poloxamer surfactant; up to about 150 mM of sodium chloride, about 1 to about 30 mM sodium phosphate; and about 0 to 5 wt % sucrose or trehalose or combination thereof; wherein the composition has a pH of about 6.0 to about pH 7.0, and more preferably about 6.0 to about 6.6 and most preferably about 6.3 to about 6.5.

The surfactant/sodium chloride stabilized composition is preferably characterized by SEC analysis at $T_2$ in which: monomer content is greater than about 80 wt. %; aggregate(s) content is less than about 3 wt %, and fragment 3 content is about 8 wt. %.

The sodium chloride-stabilized etanercept composition is preferably characterized by:
  (a) an SEC analysis at $T_4$ of greater than about 90, 91, 92, 93, 94, 95, 96, or 97 wt % monomer content; and less than about 3, 2 or 1 wt % aggregate(s) content; and
  (b) an HIC analysis at $T_2$ wherein the amount of the composition represented by peak 1 of the HIC chromatogram is less than about 4, 3, 2 or 1 wt %; the amount of the composition represented by peak 2 of the HIC chromatogram is greater than 80, 81, 82, 83, 84 85 or 86 wt %; and the amount of the composition represented by peak 3 of the HIC chromatogram is less than about 20, 19, 18, 17, 16, 15, 14, or 13 wt %; and
  (c) an HIC analysis at $T_4$ wherein the amount of the composition represented by peak 1 of the HIC chromatogram is less than about 3, 2 or 1 wt %; the amount of the composition represented by peak 2 of the HIC chromatogram is greater than 80, 81, 82, 83, 84 or 85 wt %; and the amount of the composition represented by peak 3 of the HIC chromatogram is less than 20, 19, 18, 17, 16, 15, 14 or 13 wt %.

In a further embodiment, preferred composition using surfactant plus sodium chloride for stabilization comprise up to about 150 mM sodium chloride, about 1 to 30 mM sodium phosphate, and about 0-5 wt. % sucrose or trehalose, or combination of sucrose and trehalose and having a pH of about 6.0 to 6.6; and characterized by: an SEC analysis at $T_4$ of greater than about 95 wt. % monomer content and less than about 1 wt % aggregate(s) content; an HIC analysis at $T_2$ wherein the amount of the composition represented by peak 1 of the HIC chromatogram is less than or equal to about 3 wt %; the amount of the composition represented by peak 2 of the HIC chromatogram is greater than about 82 wt %; and the amount of the composition represented by peak 3 of the HIC chromatogram is less than about 15 wt %; and an HIC analysis at $T_4$ wherein the amount of the composition represented by peak 1 of the HIC chromatogram is less than about 2 wt %; the amount of the composition represented by peak 2 of the HIC chromatogram is greater than about 84 wt %; and the amount of the composition represented by peak 3 of the HIC chromatogram is less than or equal to about 14 wt %.

Particularly preferred compositions in terms of reduced aggregates and fragments are those in which the surfactant/sodium chloride stabilized etanercept formulations exhibit HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt. % and preferably greater than about 99 wt %; and the amount of the composition represented by peak 3 of the HIC chromatogram is less than about 1 wt %.

In a further embodiment of the invention, an NaCl stabilized etanercept formulation contains up to about 5 mM arginine.

In the above-referenced NaCl stabilized etanercept formulations, the terms "SEC", "$T_2$" "$T_4$" "HIC" "monomer content" "aggregate(s)" and "fragment 3" "peak 1," "peak 2," and "peak 3," are defined in the examples below.

Surfactants for Reduced Sub-Visible Particles

As noted above, the invention employs surfactants, preferably polysorbate surfactants or poloxamer surfactants, to achieve a marked reduction in the formation of subvisible particles in an etanercept formulation. While the invention contemplates the use of any surfactant, and any polysorbate or poloxamer surfactant, the preferred surfactants for use in the invention are polysorbate 80 and Pluronic F-68, both of which readily commercially available. The invention may be practiced using the surfactant additives to achieve reductions in sub-visible particles with or without the additional stabilizing ingredients described in the embodiments above. The present invention is based in part on our surprising and unexpected discovery that the presence surfactants can afford a dramatic reduction in sub-visible particles in etanercept formulations, in comparison to formulations lacking such surfactants.

Polysorbate surfactants contemplated for use herein are derived from polyethoxylated sorbitan. Polysorbate 80, (also known as polyoxyethylene-sorbitan-20 mono-oleate) is also commercially available as "Tween 80" and is particularly preferred for use in the present invention. Polysorbate 20, 40 and 60 may also be used.

The poloxamer surfactants contemplated for use herein are well known in the pharmaceutical formulation art, and consist of block copolymers based on ethylene oxide and propylene oxide and may be commercially obtained from BASF. For example, BASF markets the poloxamers known commercially as Pluronic F-68 and which is particularly preferred for use in the present invention.

The amount of polysorbate or poloxamer useful in the etanercept formulations of the present invention is added to the formulations in the range of 0.0005% to 1% (w/v); preferably within the range of about 0.005% to about 0.1% (w/v), and most preferably in the range of about 0.01 to about 0.05% (w/v), of the formulation.

Additional Components of the Provided Pharmaceutical Compositions

The formulations of the invention may also include buffers, tonicity modifiers, excipients, pharmaceutically acceptable carriers and other commonly used inactive ingredients of the pharmaceutical compositions. For simplicity, these are discussed more fully later in the application.

Buffers maintain pH in a desired range. Suitable buffers include histidine, potassium phosphate, sodium or potassium citrate, maleic acid, ammonium acetate, tris-(hydroxymethyl)-aminomethane (tris), various forms of acetate and diethanolamine. The concentration of the buffer in the formulation is preferably between about 1 mM to about 1M, and more preferably about 10 mM to about 200 mM. Buffers are well known in the art and are manufactured by known methods and available from commercial suppliers.

Examples of suitable buffers are phosphate, histidine, citrate, maleate, tartrate, succinate, acetate, tris-(hydroxymethyl)-aminomethane (tris), bicarbonate.

In a preferred embodiment, the buffer is sodium phosphate.

In a preferred embodiment, the pH of the pharmaceutical composition is at or near physiological levels. Thus, preferably, the pH of the provided compositions is between about 5.8 and about 8.4; and even more preferably, between about 6.2 and about 7.4. A person of ordinary skill in the art will understand that the pH can be adjusted as necessary to maximize stability and solubility of etanercept in a particular formulation. Thus, etanercept formulations at a pH outside of physiological ranges, yet tolerable to the patient, are also within the scope of the invention.

A tonicity modifier is a molecule that contributes to the osmolality of a solution. The osmolality of a pharmaceutical composition is preferably adjusted to maximize the active ingredient's stability and/or to minimize discomfort to the patient upon administration. It is generally preferred that a pharmaceutical composition be isotonic with serum, i.e., having the same or similar osmolality, which is achieved by addition of a tonicity modifier.

In a preferred embodiment, the osmolality of the provided formulations is from about 180 to about 420 mOsM. However, it is to be understood that the osmolality can be either higher or lower as specific conditions require.

Examples of tonicity modifiers suitable for modifying osmolality include, but are not limited to amino acids (not including arginine) (e.g., cysteine, histidine and glycine), salts (e.g., sodium chloride, potassium chloride and sodium citrate) and/or saccharides (e.g., sucrose, glucose and mannitol).

Preferred tonicity modifiers are glycine, alanine, sodium chloride, potassium chloride, and sodium sulfate.

In a preferred embodiment, the concentration of the tonicity modifier in the formulation is preferably between about 1 mM to about 1 M, more preferably about 10 mM to about 200 mM. Tonicity modifiers are well known in the art and are manufactured by known methods and available from commercial suppliers.

Excipients, also referred to as chemical additives, co-solutes, or co-solvents, that stabilize the polypeptide while in solution (also in dried or frozen forms) can also be added to a pharmaceutical composition. Excipients are well known in the art and are manufactured by known methods and available from commercial suppliers.

Examples of suitable excipients include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, poly(viny alcohol) PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols, (e.g., PEG, and glycerol) and dimethylformamide (DMF); amino acids such as: proline, L-serine, sodium glutamic acid, alanine, glycine, lysine hydrochloride, sarcosine and gamma-aminobutyric acid; and miscellaneous excipients such as: potassium phosphate, sodium acetate, ammonium sulfate, magnesium sulfate, sodium sulfate, trimethylamine N-oxide, betaine, metal ions (e.g., zinc, calcium, and magnesium), CHAPS, monolaurate, 2-O-beta-mannoglycerate or any combination of the above.

Preferred excipients are sucrose, lactose, glycerol, xylitol, sorbitol, mannitol, maltose, inositol, trehalose, glucose, bovine serum albumin (BSA), human serum albumin (HSA), recombinant albumin, dextran, PVA, hydroxypropyl methylcellulose (HPMC), polyethyleneimine, gelatin, polyvinylpyrrolidone (PVP), hydroxyethylcellulose (HEC), polyethylene glycol, ethylene glycol, glycerol, alanine, glycine, lysine hydrochloride, sarcosine, SDS, trimethylamine N-oxide, betaine, zinc ions, calcium ions, magnesium ions, CHAPS, sucrose monolaurate, and 2-O-beta-mannoglycerate.

The concentration of one or more excipients in a formulation of the invention is/are preferably between about 0.001 to 5 weight percent, more preferably about 0.1 to 2 weight percent.

Methods of Treatment

In another embodiment, the invention provides a method of treating a mammal comprising administering a therapeutically effective amount of the pharmaceutical compositions of the invention to a mammal, wherein the mammal has a disease or disorder that can be beneficially treated with etanercept.

In a preferred embodiment, the etanercept is derived from the same species of mammal as is to be treated with the composition.

In a preferred embodiment, the mammal is a human.

Diseases or disorders that can be treated with the provided compositions include but are not limited to rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, and atopic dermatitis. Additional diseases or disorders that can be treated with the compositions of the present invention include those described in WO 00/62790, WO 01/62272, U.S. Patent Application No. 2001/0021380, and U.S. Pat. No. 7,648,702 B2, the relevant portions of which are incorporated herein by reference.

The provided pharmaceutical compositions may be administered to a subject in need of treatment by injection systemically, such as by intravenous injection; or by injection or application to the relevant site, such as by direct injection, or direct application to the site when the site is exposed in surgery; or by topical application.

In one embodiment, the invention provides a method of treatment and/or prevention of rheumatoid arthritis comprises administering to a mammal in need thereof a therapeutically effective amount of one of the provided etanercept compositions.

The therapeutically effective amount of the etanercept in the provided compositions will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations.

In one embodiment, the effective etanercept amount per adult dose is from about 1-500 mg/m$^2$, or from about 1-200 mg/m$^2$, or from about 1-40 mg/m$^2$ or about 5-25 mg/m$^2$.

Alternatively, a flat dose may be administered, whose amount may range from 2-500 mg/dose, 2-100 mg/dose or from about 10-80 mg/dose.

If the dose is to be administered more than one time per week, an exemplary dose range is the same as the foregoing described dose ranges or lower and preferably administered two or more times per week at a per dose range of 25-100 mg/dose.

In another embodiment, an acceptable dose for administration by injection contains 80-100 mg/dose, or alternatively, containing 80 mg per dose.

The dose can be administered weekly, biweekly, or separated by several weeks (for example 2 to 8).

In one embodiment, etanercept is administered at 25 to 75 mg/ml by a single subcutaneous (SC) injection.

In some instances, an improvement in a patient's condition will be obtained by administering a dose of up to about 100 mg of the pharmaceutical composition one to three times per week over a period of at least three weeks. Treatment for longer periods may be necessary to induce the desired degree of improvement. For incurable chronic conditions the regimen may be continued indefinitely. For pediatric patients (ages 4-17), a suitable regimen may involve administering a dose of 0.4 mg/kg to 5 mg/kg of etanercept, one or more times per week.

In another embodiment, the pharmaceutical formulations of the invention may be prepared in a bulk formulation, and as such, the components of the pharmaceutical composition are adjusted to be higher than would be required for administration and diluted appropriately prior to administration.

The pharmaceutical compositions can be administered as a sole therapeutic or in combination with additional therapies as needed. Thus, in one embodiment, the provided methods of treatment and/or prevention are used in combination with administering a therapeutically effective amount of another active agent. The other active agent may be administered before, during, or after administering the pharmaceutical compositions of the present invention. Another active agent may be administered either as a part of the provided compositions, or alternatively, as a separate formulation.

Administration of the provided pharmaceutical compositions can be achieved in various ways, including parenteral, oral, buccal, nasal, rectal, intraperitoneal, intradermal, transdermal, subcutaneous, intravenous, intra-arterial, intracardiac, intraventricular, intracranial, intratracheal, intrathecal administration, intramuscular injection, intravitreous injection, and topical application.

The pharmaceutical compositions of this invention are particularly useful for parenteral administration, i.e., subcutaneously, intramuscularly, intravenously, intraperitoneal, intracerebrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e.g., Inject-Ease®, Genject®, injector pens such as GenPen®, and needleless devices such as MediJector® and BioJector®. The present pharmaceutical composition can also be adapted for yet to be discovered administration methods. See also Langer, 1990, Science, 249:1527-1533.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

In another embodiment, the present invention is directed to a kit or container, which contains an aqueous pharmaceutical composition of the invention. The concentration of the polypeptide in the aqueous pharmaceutical composition can vary over a wide range, but is generally within the range of from about 0.05 to about 20,000 micrograms per milliliter (μg/ml) of aqueous formulation. The kit can also be accompanied by instructions for use.

The present invention is more particularly described in the following examples that are intended as illustrative only, since many modifications and variations therein will be apparent to those skilled in the art. In the following examples it should be understood that weight percentages of various ingredients are expressed as w/v percentages.

Example 1A

Etanercept Stabilized with Surfactant Plus Serine

A stable aqueous pharmaceutical composition containing etanercept and stabilized with surfactant and serine (without arginine) was prepared as follows:

Each formulation component (buffer, amino acid, sugar, polyol, surfactant etc) is weighed to the amount required for a given volume of formulation buffer. These components are combined into a beaker or vessel capable of carrying and measuring the given volume of formulation buffer. A volume of deionized water equal to approximately ¾ of the target given formulation buffer is added to the beaker, and the components solubilized through use of a magnetic stir bar. The pH of the buffer is adjusted to the target formulation pH using 1 molar sodium hydroxide and/or 1 molar hydrogen chloride. The final formulation buffer volume is then raised to the target volume through the addition of deionized water. The solution is mixed with a magnetic stir bar after final water addition. Etanercept protein solution is placed in dialysis material housing (such as Thermo Scientific Slide-A-Lyzer MINI Dialysis Unit 10,000 MWCO), which is then placed in contact with the desired formulation buffer for 12 hours at 4° C. Formulation buffer volume to protein solution volume ratio should be no less than 1000:1. The dialysis housing and protein solution it contains is then placed in a second, equal volume of formulation buffer for an additional 12 hours at 4° C.

Resulting protein solution is removed from the dialysis material housing, and the concentration of protein determined using ultraviolet spectroscopy. Protein concentration is adjusted to the desired level using centrifugation (such as Amicon Ultra 10,000 MWCO Centrifugal Concentrators) and/or dilution with formulation buffer.

Five sample compositions of the invention in which etanercept is stabilized with serine (in the absence of arginine) are represented Formulation 1:15

| Ingredient | concentration |
| --- | --- |
| Etanercept (active ingredient) | 50 mg/ml |
| Serine (inactive ingredient) | 25 mM |
| Sodium phosphaye, pH 6.3 (inactive) | 25 mM |
| Sucrose (inactive) | 1% (w/v) |
| NaCl (inactive) | 100 mM |
| Polysorbate 80 | .02% (w/v) |

Formulation 1:12

| Ingredient | concentration |
| --- | --- |
| Etanercept (active ingredient) | 50 mg/ml |
| Serine (inactive ingredient) | 25 mM |
| Sodium phosphate, pH 6.4 (inactive) | 25 mM |
| Sucrose (inactive) | 2.5% (w/v) or 5% (w/v) |
| NaCl (inactive) | 100 mM |
| Polysorbate 80 | .02% (w/v) |

Formulation 1:16

| Ingredient | concentration |
| --- | --- |
| Etanercept (active ingredient) | 50 mg/ml |
| Serine (inactive ingredient) | 50 mM |
| Sodium phosphaye, pH 6.4 (inactive) | 25 mM |
| Sucrose (inactive) | 5% (w/v) |
| NaCl (inactive) | 25 mM |
| Polysorbate 80 | .02% (w/v) |

Formulation 2:4

| Ingredient | concentration |
| --- | --- |
| Etanercept (active ingredient) | 50 mg/ml |
| Serine (inactive ingredient) | 100 mM |
| Sodium phosphaye, pH 6.3 (inactive) | 25 mM |

-continued

| Ingredient | concentration |
| --- | --- |
| Sucrose (inactive) | 1% (w/v) |
| Polysorbate 80 | .02% (w/v) |

Formulation 3:8

| Ingredient | concentration |
| --- | --- |
| Etanercept (active ingredient) | 50 mg/ml |
| Serine (inactive ingredient) | 120 mM |
| Sodium phosphaye, pH 6.3 (inactive) | 25 mM |
| Sucrose (inactive) | 1% (w/v) |
| Polysorbate 80 | .02% (w/v) |

The compositions can be tested for long-term stability by size exclusion chromatography (SEC), denatured SEC (dSEC), hydrophobic interaction chromatography (HIC), sodium dodecylsulfate polyacrylamide gel electrophoresis (SDS-PAGE), and for binding and bioactivity at various timepoints. The bioactivity can be measured by any number of well-known assays including by SEC, dSEC, HIC, as discussed below. Flow cam analysis can be used to evaluate sub-visible particles.

For example, the techniques of Size Exclusion Chromatography are described in Hawe et al, Pharm. Res. 2011, 28: 2302 and/or van Marrschalkerweerd et al., Eur. J. Pharm. Biopharm. 2011, 78: 213. Similarly, the techniques of Denatured Size Exclusion Chromatography, Hydrophobic Interaction Chromatography, and Sodium DodecylSulfate-Poly-Acrylamide Gel Electrophoresis are also well known to persons having ordinary skill in the art.

It is believed that the composition will be stable over the term of two years or more.

Example 1B

Etanercept Stabilized with Surfactant Plus Proline

Compositions stabilized with surfactant plus proline in this Example 1B may be prepared and tested using the procedures similar to those described in Example 1A. Etanercept formulations using surfactant plus proline for stabilization, exemplified below, do not contain arginine.

Formulation 1:4

| Ingredient | concentration |
| --- | --- |
| Etanercept (active ingredient) | 50 mg/ml |
| Proline (inactive ingredient) | 25 mM |
| Sodium phosphate, pH 6.3 (inactive) | 25 mM |
| Sucrose (inactive) | 2.5% (w/v) |
| NaCl (inactive) | 50 mM |
| Polysorbate 80 | .02% (w/v) |

Formulation 1:5

| Ingredient | concentration |
| --- | --- |
| Etanercept (active ingredient) | 50 mg/ml |
| Proline (inactive ingredient) | 50 mM |
| Sodium phosphate, pH 6.3 (inactive) | 25 mM |
| Sucrose (inactive) | 1.0% (w/v) |
| NaCl (inactive) | 25 mM |
| Polysorbate 80 | .02% (w/v) |

Formulation 1:6

| Ingredient | concentration |
| --- | --- |
| Etanercept (active ingredient) | 50 mg/ml |
| Proline (inactive ingredient) | 100 mM |
| Sodium phosphate, pH 6.3 (inactive) | 25 mM |
| Sucrose (inactive) | 1.0% (w/v) |
| Polysorbate 80 | .02% (w/v) |

The compositions can be tested for long-term stability, and the bioactivity can be measured in the same fashion as discussed in Example 1A. Flow cam analysis can be used to evaluate sub-visible particles.

It is believed that the compositions will be stable over the term of two years or more.

Example 1C

Etanercept Stabilized with Surfactant Plus Glutamate

Compositions stabilized with surfactant plus glutamate may be prepared and tested using the procedures similar to those described in Example 1A.

Surfactant/Glutamate stabilized etanercept compositions, containing no arginine, are exemplified below:

Formulation 1:9

| Ingredient | concentration |
| --- | --- |
| Etanercept (active ingredient) | 50 mg/ml |
| Glutamate (inactive ingredient) | 25 mM |
| Sodium phosphate, pH 6.3 (inactive) | 25 mM |
| Sucrose (inactive) | 1% (w/v) |
| NaCl (inactive) | 100 mM |
| Polysorbate 80 | .02% (w/v) |

Formulation 2:2

| Ingredient | concentration |
| --- | --- |
| Etanercept (active ingredient) | 50 mg/ml |
| Glutamate (inactive ingredient) | 50 mM |
| Sodium phosphate, pH 6.3 (inactive) | 25 mM |
| Sucrose (inactive) | 1% (w/v) |
| NaCl (inactive) | 50 mM |
| Polysorbate 80 | .02% (w/v) |

Formulation 2:3

| Ingredient | concentration |
| --- | --- |
| Etanercept (active ingredient) | 50 mg/ml |
| Glutamate (inactive ingredient) | 100 mM |
| Sodium phosphate, pH 6.3 (inactive) | 25 mM |
| Sucrose (inactive) | 1% (w/v) |
| Polysorbate 80 | .02% (w/v) |

Formulation 3:5

| Ingredient | concentration |
| --- | --- |
| Etanercept (active ingredient) | 50 mg/ml |
| Glutamate (inactive ingredient) | 120 mM |
| Sodium phosphate, pH 6.5 (inactive) | 25 mM |
| Sucrose (inactive) | 1% (w/v) |
| Polysorbate 80 | .02% (w/v) |

The composition can be tested for long-term stability, and the bioactivity can be measured in the same fashion as discussed in Example 1A. Flow cam analysis can be used to evaluate sub-visible particles.

It is believed that the composition will be stable over the term of two years or more.

Example 2A

Etanercept Stabilized with Surfactant Plus Calcium Chloride

Etanercept formulations stabilized with surfactant plus calcium chloride may be prepared and tested using the procedures similar to those described in Example 1A.

Etanercept compositions stabilized with surfactant plus calcium chloride, and containing no arginine, are exemplified below.

Formulation P1:1

| Ingredient | concentration |
| --- | --- |
| Etanercept (active ingredient) | 50 mg/ml |
| Calcium chloride (inactive ingredient) | 2 mM |
| Sodium phosphate, pH 6.3 (inactive) | 25 mM |
| Polysorbate 80 | .02% (w/v) |

Formulation 1:11

| Ingredient | concentration |
| --- | --- |
| Etanercept (active ingredient) | 50 mg/ml |
| Calcium chloride (inactive ingredient) | 2 mM |
| Sodium phosphate, pH 6.3 (inactive) | 25 mM |
| NaCl (inactive) | 100 mM |
| Sucrose (inert) | 2.5% (w/v) |
| Polysorbate 80 | .02% (w/v) |

Formulation 1:18

| Ingredient | concentration |
| --- | --- |
| Etanercept (active ingredient) | 50 mg/ml |
| Calcium chloride (inactive ingredient) | 2 mM |
| Sodium phosphate, pH 6.3 (inactive) | 25 mM |
| Xylitol (inactive) | 10 mM |
| Polysorbate 80 | .02% (w/v) |

Formulation 3:6

| Ingredient | concentration |
| --- | --- |
| Etanercept (active ingredient) | 50 mg/ml |
| Calcium chloride (inactive ingredient) | 2 mM |
| Sodium phosphate, pH 6.3 (inactive) | 15 mM |
| NaCl (inactive) | 75 mM |
| Sucrose (inactive) | 3% (w/v) |
| Polysorbate 80 | .02% (w/v) |

Formulation 3:9

| Ingredient | concentration |
| --- | --- |
| Etanercept (active ingredient) | 50 mg/ml |
| Calcium chloride (inactive ingredient) | 1 mM |
| Sodium phosphate, pH 6.6 (inactive) | 10 mM |
| NaCl (inactive) | 50 mM |
| Trehalose (inactive) | 5% (w/v) |
| Polysorbate 80 | .02% (w/v) |

The composition can be tested for long-term stability, and the bioactivity can be measured in the same fashion as discussed in Example 1A. Flow cam analysis can be used to evaluate sub-visible particles.

It is believed that the composition will be stable over the term of two years or more.

Example 2B

Etanercept Stabilized with Surfactant Plus Magnesium Chloride

Etanercept formulations stabilized with surfactant plus magnesium chloride may be prepared and tested using the procedures similar to those described in Example 1A. The etanercept formulations exemplified below do not contain arginine.

Formulation P1:2

| Ingredient | concentration |
| --- | --- |
| Etanercept (active ingredient) | 50 mg/ml |
| Magnesium chloride (inactive ingredient) | 2 mM |
| Sodium phosphate, pH 6.3 (inactive) | 25 mM |
| Polysorbate 80 | .02% (w/v) |

Formulation 2:15

| Ingredient | concentration |
|---|---|
| Etanercept (active ingredient) | 50 mg/ml |
| Magnesium chloride (inactive ingredient) | 4 mM |
| Sodium phosphate, pH 6.4 (inactive) | 25 mM |
| NaCl (inactive) | 100 mM |
| Sucrose (inactive) | 2.5% (w/v) |
| Polysorbate 80 | .02% (w/v) |

Formulation 3:7

| Ingredient | concentration |
|---|---|
| Etanercept (active ingredient) | 50 mg/ml |
| Magnesium chloride (inactive ingredient) | 5 mM |
| Sodium phosphate, pH 6.3 (inactive) | 15 mM |
| NaCl (inactive) | 75 mM |
| Sucrose (inactive) | 2.5% (w/v) |
| Polysorbate 80 | .02% (w/v) |

Formulation 3:14

| Ingredient | concentration |
|---|---|
| Etanercept (active ingredient) | 50 mg/ml |
| Magnesium chloride (inactive ingredient) | 10 mM |
| Sodium phosphate, pH 6.3 (inactive) | 25 mM |
| NaCl (inactive) | 110 mM |
| Sucrose (inactive) | 1% (w/v) |
| Polysorbate 80 | .02% (w/v) |

Formulation 4:2

| Ingredient | concentration |
|---|---|
| Etanercept (active ingredient) | 50 mg/ml |
| Magnesium chloride (inactive ingredient) | 10 mM |
| Sodium phosphate, pH 6.5 (inactive) | 15 mM |
| NaCl (inactive) | 75 mM |
| Sucrose (inactive) | 3% (w/v) |
| Polysorbate 80 | .02% (w/v) |

The composition can be tested for long-term stability, and the bioactivity can be measured in the same fashion as discussed in Example 1A. Flow cam analysis can be used to evaluate sub-visible particles.

It is believed that the composition will be stable over the term of two years or more.

Example 2C

Etanercept Stabilized with Surfactant Plus Zinc Chloride

Etanercept formulations stabilized with surfactant plus zinc chloride may be prepared and tested using the procedures similar to those described in Example 1A.

The etanercept formulation exemplified below does not contain arginine.

Formulation P1:3

| Ingredient | concentration |
|---|---|
| Etanercept (active ingredient) | 50 mg/ml |
| Zinc chloride (inactive ingredient) | 2 mM |
| Sodium phosphate, pH 6.3 (inactive) | 25 mM |
| Polysorbate 80 | .02% (w/v) |

The composition can be tested for long-term stability, and the bioactivity can be measured in the same fashion as discussed in Example 1A. Flow cam analysis can be used to evaluate sub-visible particles.

It is believed that the composition will be stable over the term of two years or more.

Example 3A

Etanercept Stabilized with Surfactant Plus Meglumine

Etanercept compositions stabilized with surfactant plus meglumine may be prepared and tested using the procedures similar to those described in Example 1A. Surfactant/meglumine stabilized etanercept compositions, exemplified below, do not contain arginine.

Formulation 1:19

| Ingredient | concentration |
|---|---|
| Etanercept (active ingredient) | 50 mg/ml |
| Meglumine (inactive ingredient) | 5% (w/v) |
| Sodium phosphate, pH 6.3 (inactive) | 25 mM |
| Polysorbate 80 | .02% (w/v) |

Formulation 1:21

| Ingredient | concentration |
|---|---|
| Etanercept (active ingredient) | 50 mg/ml |
| Meglumine (inactive ingredient) | 0.49% (w/v) |
| Sodium phosphate, pH 6.3 (inactive) | 25 mM |
| Sucrose (inactive) | 1% (w/v) |
| NaCl (inactive) | 100 mM |
| Polysorbate 80 | .02% (w/v) |

The composition can be tested for long-term stability, and the bioactivity can be measured in the same fashion as discussed in Example 1A. Flow cam analysis can be used to evaluate sub-visible particles.

It is believed that the composition will be stable over the term of two years or more.

Example 3B

Etanercept Stabilized with a Surfactant Plus Derivative of Mannitol

Etanercept compositions stabilized with a derivative of mannitol may be prepared and tested using the procedures similar to those described in Example 1A.

The formulation exemplified below does not contain arginine:

| Ingredient | % by weight |
|---|---|
| Etanercept (active ingredient) | 50 mg/ml |
| Mannosylglycerate (inactive ingredient) | 4% (w/v) |
| Polysorbate 80 | .02% (w/v) |

The composition can be tested for long-term stability, and the bioactivity can be measured in the same fashion as discussed in Example 1A. Flow cam analysis can be used to evaluate sub-visible particles.

It is believed that the composition will be stable over the term of two years or more.

Example 4A

Etanercept Stabilized with Surfactant Plus Trehalose (or Sucrose) and Mannitol

Etanercept compositions stabilized with mannitol in combination with trehalose (or sucrose), may be prepared and tested using the procedures similar to those described in Example 1A. The stabilized formulations exemplified below do not contain arginine.

Formulation P1:5

| Ingredient | concentration |
|---|---|
| Etanercept (active ingredient) | 50 mg/ml |
| Trehalose (inactive ingredient) | 4% (w/v/) |
| Mannitol (inactive) | 2% (w/v/) |
| Polysorbate 80 | .02% (w/v) |

Formulation 1:10

| Ingredient | concentration |
|---|---|
| Etanercept (active ingredient) | 50 mg/ml |
| Sodium phosphate, pH 6.32 (inactive) | 25 mM |
| Sucrose (inactive) | 5% (w/v) |
| Mannitol (inactive) | 2% (w/v/) |
| Polysorbate 80 | .02% (w/v) |

The composition can be tested for long-term stability, and the bioactivity can be measured in the same fashion as discussed in Example 1A. Flow cam analysis can be used to evaluate sub-visible particles.

It is believed that the composition will be stable over the term of two years or more.

Example 4B

Etanercept Stabilized with Surfactant Plus Sucrose and Sorbitol

Etanercept compositions stabilized with a combination of surfactant plus sucrose and sorbitol may be prepared and tested using the procedures similar to those described in Example 1A. The formulation exemplified below does not contain arginine.

| Ingredient | concentration |
|---|---|
| Etanercept (active ingredient) | 50 mg/ml |
| Sucrose (inactive ingredient) | 4% (w/v) |
| Sorbitol (inactive) | 2% (w/v) |
| Sodium phosphate, pH 6.3 (inactive) | 25 mM |
| Polysorbate 80 | .02% (w/v) |

The composition can be tested for long-term stability, and the bioactivity can be measured in the same fashion as discussed in Example 1A. Flow cam analysis can be used to evaluate sub-visible particles.

It is believed that the composition will be stable over the term of two years or more.

The foregoing description of the exemplary embodiments of the invention has been presented only for the purposes of illustration and description and is not intended to be exhaustive or to limit the invention to the precise forms disclosed. Many modifications and variations are possible in light of the above teaching.

Example 5

Etanercept Stabilized with Surfactant Plus Xylitol

Etanercept formulations stabilized with surfactant plus xylitol may be prepared and tested using the procedures similar to those described in Example 1A. The compositions exemplified below do not contain arginine.

Formulation 1:17

| Ingredient | concentration |
|---|---|
| Etanercept (active ingredient) | 50 mg/ml |
| Sodium phosphate, pH 6.3 (inactive) | 25 mM |
| Xylitol (inactive) | 10% (w/v) |
| Polysorbate 80 | .02% (w/v) |

Formulation 2:10

| Ingredient | concentration |
|---|---|
| Etanercept (active ingredient) | 50 mg/ml |
| Sodium phosphate, pH 6.31 (inactive) | 25 mM |
| Xylitol (inactive) | 6% (w/v) |
| Polysorbate 80 | .02% (w/v) |

Formulation 2:11

| Ingredient | concentration |
|---|---|
| Etanercept (active ingredient) | 50 mg/ml |
| Sodium phosphate, pH 6.3 (inactive) | 25 mM |
| Xylitol (inactive) | 2.5% (w/v) |
| Sucrose (inactive ingredient) | 5% (w/v) |
| Polysorbate 80 | .02% (w/v) |

Formulation 2:18

| Ingredient | concentration |
| --- | --- |
| Etanercept (active ingredient) | 50 mg/ml |
| Sodium phosphate, pH 6.4 (inactive) | 25 mM |
| Xylitol (inactive) | 2.5% (w/v) |
| Meglumine (inactive) | 2.5% (w/v) |
| Polysorbate 80 | .02% (w/v) |

Formulation 2:19

| Ingredient | concentration |
| --- | --- |
| Etanercept (active ingredient) | 50 mg/ml |
| Sodium phosphate, pH 6.24 (inactive) | 10 mM |
| Xylitol (inactive) | 2.5% (w/v) |
| Meglumine (inactive) | 2.5% (w/v) |
| NaCl (inactive) | 2.5% (w/v) |
| Sucrose (inactive) | 1% (w/v) |
| Polysorbate 80 | .02% (w/v) |

Example 6

Etanercept Stabilized with Surfactant and NaCl

Etanercept formulations stabilized with surfactant and NaCl, alone, or NaCl in combination with sucrose, trehalose and/or arginine, may be prepared and tested using the procedures similar to those described in Example 1A. With the exception of formulation 3:13 below, the compositions exemplified below do not contain arginine.

Formulation 2:8

| Ingredient | concentration |
| --- | --- |
| Etanercept (active ingredient) | 50 mg/ml |
| Sodium phosphate, pH 6.32 (inactive) | 25 mM |
| NaCl (inactive) | 150 mM |
| Polysorbate 80 | .02% (w/v) |

Formulation 2:6

| Ingredient | concentration |
| --- | --- |
| Etanercept (active ingredient) | 50 mg/ml |
| Sodium phosphate, pH 6.3 (inactive) | 15 mM |
| NaCl (inactive) | 100 mM |
| Sucrose (inactive) | 2% (w/v) |
| Polysorbate 80 | .02% (w/v) |

Formulation 3:10

| Ingredient | concentration |
| --- | --- |
| Etanercept (active ingredient) | 50 mg/ml |
| Sodium phosphate, pH 6.57 (inactive) | 10 mM |
| NaCl (inactive) | 75 mM |
| Sucrose (inactive) | 3% (w/v) |
| Polysorbate 80 | .02% (w/v) |

Formulation 3:11

| Ingredient | concentration |
| --- | --- |
| Etanercept (active ingredient) | 50 mg/ml |
| Sodium phosphate, pH 6.30 (inactive) | 25 mM |
| NaCl (inactive) | 75 mM |
| Trehalose (inactive) | 3% (w/v) |
| Polysorbate 80 | .02% (w/v) |

Formulation 3:12

| Ingredient | concentration |
| --- | --- |
| Etanercept (active ingredient) | 50 mg/ml |
| Sodium phosphate, pH 6.3 (inactive) | 25 mM |
| NaCl (inactive) | 75 mM |
| Sucrose (inactive) | 3% (w/v) |
| Polysorbate 80 | .02% (w/v) |

Formulation 3:13

| Ingredient | concentration |
| --- | --- |
| Etanercept (active ingredient) | 50 mg/ml |
| Sodium phosphate, pH 6.3 (inactive) | 25 mM |
| NaCl (inactive) | 120 mM |
| Sucrose (inactive) | 1% (w/v) |
| Arginine (inactive) | 5 mM |
| Polysorbate 80 | .02% (w/v) |

The compositions can be tested for long-term stability, and the bioactivity can be measured in the same fashion as discussed in Example 1A. Flow cam analysis can be used to evaluate sub-visible particles.

Analysis of Etanercept Formulations

A. Thermal Stability Storage

Following dialysis and concentration, samples of the etanercept formulations exemplified above were sterile filtered in a bio safety cabinet. Using sterilized pipettes and autoclaved pipette tips, samples of the etanercept formulations were transferred to pre-labeled and autoclaved 1 mL lyophilization vials. Vials were stopped with sterile butyl stoppers and crimped with aluminum caps. All vials were then transferred to thermal stability ovens. Samples were subject to two thermal stability regimes: (1) two weeks at 40° C. and (2) four weeks at 25° C. Throughout this specification, these two temperature regimes are denoted "$T_2$" and $T_4$," respectively.

B. Size Exclusion Chromatography (SEC)

Etanercept formulations disclosed herein were analyzed using the well known technique of Size Exclusion Chromatography (SEC), a high-performance liquid chromatography method in which analytes are separated by size (see Rogner, M. (2000). Size Exclusion Chromatography. *Protein Liquid Chromatography*. M. Kastner. Amsterdam, Elsevier. 61: 89-145.). In order to evaluate thermal stability of the Etanercept samples decribed above, the samples were examined by a SEC method based on the literature (van Maarschalkerweerd, A., G. J. Wolbink, et al. (2011). "Comparison of analytical methods to detect instability of etanercept during thermal stress testing." *European Journal of Pharmaceutics and Biopharmaceutics* 78(2): 213-221.) The mobile phase buffer was prepared to contain 50 mM sodium phosphate monobasic monohydrate and 150 mM arginine. The pH was adjusted to 6.5 using 1 M HCl. All separations were performed using a Tosoh TSK-Gel SWxl 6 mm×4 cm guard column (cat. no. 8543) attached linearly to a Tosoh TSK-Gel G4000 SWxl 7.8 mm×30 cm (cat. no. 8542). To perform a separation, the columns were brought to room temperature (23° C.) and equilibrated with mobile phase at a flow rate of 0.5 mL/min. 5 microliters of 50 mg/mL etanercept formulation were injected onto the column using an autosampler. The separation was accomplished over 30 minutes at a flow rate of 0.5 mL/minute. Column eluent was monitored at a wavelength of 280 nm during this time.

C. Integration of Size Exclusion Chromatography Chromatograms

All integration was performed using Chromeleon software (Dionex). Prior to integration, the SEC chromatogram for a buffer containing no etanercept was subtracted from all chromatograms. All integration was performed between retention times of 12 minutes and 26 minutes. Several parameters were used to define a peak. The minimum area for a detected peak was set to 0.05 mAu*min. The two-dimensional sensitivity for peak detection was set to 0.01 mAu and 75 seconds. Peak shoulders were added manually using a manual integration tool. All detected peaks were manually adjusted in two steps. First, peak baselines (the bottom boundary of the peak) were adjusted to horizontal. Secondly, the vertical positions of the peak baselines were adjusted to that of the chromatogram baseline. The chromatogram baseline value was defined as the signal in absence of analyte. The signal in absence of analyte was defined as the absorbance in mAu at 12 minutes retention time.

D. SEC Fractions of Etanercept Formulations

In the SEC analysis of etanercept formulations described above, three SEC chromatography fractions were identified and studied. The fractions that were analyzed were, in the order of elution from the SEC column: (1) a very high molecular weight fraction representing aggregates of the intact etanercept TNFR:FC fusion protein likely assembled via non-covalent electrostatic attraction among intact etanercept molecules (hereinafter "aggregate(s)" or aggregate(s) content); (2) monomer content, representing the intact etanercept TNFR:FC fusion protein (hereinafter referred to as "monomer" of "monomer content"); (3) a fraction likely representing one fragment or a population of fragments of the etanercept molecule in which one portion of the TNFR: molecule fusion protein has become disassociated from the monomer; such as for example dissociation of an arm of the FC portion of the fusion protein at the hinge region of the molecule (hereinafter referred to as "Fragment 3"). The following table shows the relative amounts of Aggregates, Monomer and Fragment 3 determined by SEC analysis as described above.

E. FlowCAM® Analysis of Sub-Visible Particles.

Method development may be done using a Manuel Prime with Non-Sample procedure (liquid to liquid interphase). Pronounced mixing effects are seen in the flow cell so an alternative air gap procedure (Manual Prime with Sample) is selected for sample evaluation.

Formulations of Examples 3.5 and 4.2 were evaluated with and without PS 80 at "T0". The term "T0" as used with respect to the flowCAM analysis denotes that samples were not subjected to any appreciable thermal or storage stress (i.e, maintained at 5 C or less) and then promptly tested using the flowCAM analysis within 24 to 72 hours) after the tested formulations were prepared.

Instrumentation & Accessories

FlowCAM Instrument: Model VS1, Serial #551 with Sony SX90 camera and C70 pump with a 1 mL syringe (Fluid Imaging Technologies)

FlowCAM Software: DSP Firmware Version: 54; version 3.0.3

Flow Cell: Field of View (FOV FC80) with a depth of 80 μm and a width of 700 μm (Fluid Imaging Technologies)

Objective: 10×

Context Setting (Method & Setting Parameters)

Method: Manual Prime with Sample (air gap)

Sample Analysis: 0.200 mL volume with 0.170 mL analyzed

Flow Rate: 0.100 ml/min

Auto image rate: 22 frames per second

Efficiency: 38.7%

Run time: 1.7 minutes

Distance to Nearest

Neighbor: 0 microns

Close Hole: 5 iterations

Images: Collage image border padding of 5

Particle Segmentation: Dark Threshold 15.00, Light Threshold 15.00

Acceptable Region: Left 15, Right 1255, Top 0, Bottom 959

Camera: Shutter 8

Gain 57

Auto image rate: 22 frames per second

Flash camera delay: 100 microseconds

Flash duration: 18.5 microseconds

Diameter (ESD): Min 2.00, Max 1000.00 microns

Prior to running samples, the flow cell and objective are installed and the Field of View and Focus optimization are performed. System qualification includes running water blanks and particle size standard in multiple replicates. Prior to running samples a cleaning procedure is undertaken to ensure particle counts are at acceptable levels typically below 1000 particles/mL between samples or less than 5% of the sample particles/mL between replicate samples. The routine cleaning process uses water (Millipore Direct-Q type 1, 0.22 μm filtered, 18.2 MΩ) between cleaning agents and as a final flush prior to determining count levels. Once the particle count reaches an acceptable particle per mL level the sample is carefully pipetted into the sample tip and loaded into the flow prior to initiating the sample analysis. Run quality is determined during and immediately after each run using a series of diagnostic tools in VisualSpreadSheet including x-y capture plot (to visualize flow pattern dynamics), aspectic ratio to diameter size plot (identify stuck particles), image review during the run and image analysis at completion of run using various particle characteristics (e.g. size, circularity, length, aspect ratio). Individual particle size is determined with Fluid Imaging Technologies software measurement technique known as Equivalent Spherical Diameter (ESD). ESD is the mean feret measurement of the particle based on 36 sample measurements (conducted every 5°). A feret measurement is the perpendicular distance between parallel tangents touching opposite sides of the particle.

TABLE 1

SEC ANALYSIS OF MONOMER

| Formulation No. | $t_0$ | $t_1$ | $t_2$ |
|---|---|---|---|
| Commercial Enbrel ® (comparative) [1:2] | 98.81 | 92.58 | 87.64 |
| 1:5 | 98.38 | 91.65 | 86.89 |
| 1:9 | 98.48 | 92.05 | 86.06 |
| 1:10 | 98.25 | 91.84 | 84.51 |
| 1:11 | 98.60 | 92.08 | 89.71 |
| 1:17 | 98.02 | 93.90 | 87.53 |
| 1:18 | 98.27 | 92.89 | 88.21 |
| 1:19 | 98.10 | 91.94 | 86.06 |
| 1:21 | 98.22 | 90.78 | 85.43 |
| 2:2 | 98.11 | — | 86.92 |
| 2:3 | 98.14 | — | 88.84 |
| 2:4 | 98.12 | — | 88.16 |
| 2:6 | 98.09 | — | 87.77 |
| 2:8 | 98.07 | — | 88.38 |
| 2:10 | 98.09 | — | 87.56 |
| 2:11 | 98.10 | — | 88.03 |
| 2:15 | 98.18 | — | 88.22 |
| 2:18 | 98.10 | — | 89.19 |
| 2:19 | 98.19 | — | 89.63 |
| 3:5 | 98.35 | — | 90.75 |
| 3:6 | 98.07 | — | 90.75 |
| 3:7 | 98.09 | — | 89.60 |
| 3:8 | 98.15 | — | 89.27 |
| 3:9 | 97.90 | — | 91.44 |
| 3:10 | 98.16 | — | 89.77 |
| 3:11 | 98.32 | — | 89.87 |
| 3:12 | 98.33 | — | 90.92 |
| 3:13 | 98.18 | — | 90.74 |
| 3:14 | 98.22 | — | 90.54 |
| 4:2 | 98.62 | — | 90.47 |

Note:
Amounts reported Tables I, II and III are percentages by weight
$T_0$ = formulation maintained at 5 C. and analyzed within 24 hours of creation.
$T_1$ = formulation stored for one week at 40° C.
$T_2$ = formulation stored for two weeks at 40 C.

TABLE II

SEC ANALYSIS OF AGGREGATES

| Formulation No. | $t_0$ | $t_1$ | $t_2$ |
|---|---|---|---|
| Commercial Enbrel ® (comparative) | 0.09 | 0.59 | 1.02 |
| 1:5 | 0.23 | 0.63 | 1.01 |
| 1:9 | 0.18 | 0.67 | 2.20 |
| 1:10 | 0.26 | 0.68 | 0.82 |
| 1:11 | 0.12 | 0.50 | 0.64 |
| 1:17 | 0.31 | 0.70 | 2.17 |
| 1:18 | 0.24 | 0.65 | 1.61 |
| 1:19 | 0.26 | 0.63 | 1.50 |
| 1:21 | 0.23 | 0.64 | 1.30 |
| 2:2 | 0.29 | — | 3.53 |
| 2:3 | 0.29 | — | 2.31 |
| 2:4 | 0.29 | — | 2.29 |
| 2:6 | 0.30 | — | 1.81 |
| 2:8 | 0.30 | — | 1.42 |
| 2:10 | 0.29 | — | 2.57 |
| 2:11 | 0.31 | — | 1.68 |
| 2:15 | 0.27 | — | 1.83 |
| 2:18 | 0.29 | — | 1.53 |
| 2:19 | 0.26 | — | 1.24 |
| 3:5 | 0.28 | — | 0.99 |
| 3:6 | 0.23 | — | 1.27 |
| 3:7 | 0.28 | — | 0.93 |
| 3:8 | 0.28 | — | 1.60 |
| 3:9 | 0.37 | — | 0.73 |
| 3:10 | 0.27 | — | 1.33 |
| 3:11 | 0.20 | — | 1.24 |
| 3:12 | 0.21 | — | 0.85 |
| 3:13 | 0.28 | — | 0.86 |
| 3:14 | 0.25 | — | 0.91 |
| 4:2 | | | 1.56 |

TABLE III

ANALYSIS OF FRAGMENT 3

| Formulation No | $t_0$ | $t_1$ | $t_2$ |
|---|---|---|---|
| Commercial Enbrel ® (comparative) [1:2} | 0.00 | 3.30 | 6.29 |
| 1:5 | 0.00 | 4.43 | 6.64 |
| 1:9 | 0.00 | 3.96 | 6.34 |
| 1:10 | 0.00 | 3.78 | 8.04 |
| 1:11 | 0.00 | 3.92 | 4.71 |
| 1:17 | 0.00 | 2.33 | 4.10 |
| 1:18 | 0.00 | 3.05 | 4.65 |
| 1:19 | 0.00 | 3.82 | 6.73 |
| 1:21 | 0.00 | 4.92 | 7.37 |
| 2:2 | 0.00 | — | 4.67 |
| 2:3 | 0.00 | — | 3.61 |
| 2:4 | 0.00 | — | 3.61 |
| 2:6 | 0.00 | — | 4.73 |
| 2:8 | 0.00 | — | 6.29 |
| 2:10 | 0.00 | — | 5.10 |
| 2:11 | 0.00 | — | 5.68 |
| 2:15 | 0.00 | — | 5.56 |
| 2:18 | 0.00 | — | 4.24 |
| 2:19 | 0.00 | — | 4.34 |
| 3:5 | 0 | — | 3.15 |
| 3:6 | 0 | — | 4.72 |
| 3:7 | 0 | — | 4.37 |
| 3:8 | 0 | — | 3.61 |
| 3:9 | 0 | — | 3.48 |
| 3:10 | 0 | — | 3.76 |
| 3:11 | 0 | — | 3.59 |
| 3:12 | 0 | — | 3.68 |
| 3:13 | 0 | — | 3.88 |
| 3:14 | 0 | — | 3.83 |
| 4:2 | | | 5.40 |

TABLE IV

SEC MONOMER CONTENT
(4 weeks/25° C.)

| FORMULATION No. | $T_0$ Monomer Content | $T_4$ Monomer Content |
|---|---|---|
| Commercial Enbrel ® (comparative) | 98.15 | 97.86 |
| 3:5 | 98.35 | 95.16 |
| 3:6 | 98.07 | 94.84 |

TABLE IV-continued

SEC MONOMER CONTENT
(4 weeks/25° C.)

| | FORMULATION No. | |
|---|---|---|
| | $T_0$ Monomer Content | $T_4$ Monomer Content |
| 3:7 | 98.09 | 97.75 |
| 3:8 | 98.15 | 97.65 |
| 3:9 | 97.90 | 97.44 |
| 3:10 | 98.16 | 97.66 |
| 3:11 | 98.32 | 97.75 |
| 3:12 | 98.33 | 97.90 |
| 3:13 | 98.18 | 97.78 |
| 3:14 | 98.22 | 97.79 |
| 4:2 | 98.62 | 94.70 |

Table IV below shows monomer (etanercept) content of etanercept formulations prepared according to the present invention, when stored for four weeks at 25 C.°-denoted by the symbol $T_4$. In the following table $T_0$ represents SEC measurements conducted within 24 hours of formulation preparation, at sample temperature of 5° C.; and $T_4$ represents etanercept formulation samples subjected to SEC analysis after 4 weeks storage at 25° C.

Table V below shows aggregate(s) content of etanercept formulations prepared according to the present invention after storage for four weeks at 25 C°. In the following table $T_0$ represents SEC measurements conducted within 24 hours of formulation preparation, at sample temperature of 5° C.; and $T_4$ represents etanercept formulation samples subjected to SEC analysis after 4 weeks storage at 25° C.

TABLE V

SEC AGGREGATES CONTENT
(4 weeks/25° C.)

| | FORMULATION No. | |
|---|---|---|
| | $T_0$ Aggregate(s) Content | $T_4$ Aggregate(s) Content |
| Commercial Enbrel ® (comparative) | 0.28 | 0.25 |
| 3:5 | — | 0.50 |
| 3:6 | — | 0.57 |
| 3:7 | 0.28 | 0.31 |
| 3:8 | 0.28 | 0.37 |
| 3:9 | 0.37 | 0.41 |
| 3:10 | 0.27 | 0.32 |
| 3:11 | 0.20 | 0.27 |
| 3:12 | 0.21 | 0.26 |
| 3:13 | 0.28 | 0.32 |
| 3:14 | 0.25 | 0.28 |
| 4:2 | — | 0.57 |

HIC Analysis of Etanercept Formulations

The following tables (Tables VI and VII) show the results of hydrophobic interaction chromatography ("HIC chromatography") conducted on samples 3:5 through 3:14. HIC chromatography was carried out in the manner described in U.S. Pat. No. 7,294,481, incorporated herein by reference. Samples were evaluated at $t_0$ (within 24 hours of preparation at 5° C.) and again after either two weeks of storage at 25° C. ($t_2$) (see Table VI) or after 4 weeks of storage at 25° C. ($t_4$)(See Table VII) Peak 1 is believed to be or include "Fragment 3" referenced above in the discussion of SEC data; Peak 2 is etanercept monomer as referenced above in the discussion of SEC data; and Peak 3 represents or includes "Aggregate(s)" as referenced above in the discussion of SEC data. It should further be understood that the terms "peak 1", "peak 2" and "peak 3 as used here also constitute a reference to the HIC peak 1, peak 2 and peaks referred to and disclosed in FIG. 4 of U.S. Pat. No. 7,294,481 incorporated herein by reference.

TABLE VI

HIC Data after Two Weeks Storage at 40° C.

| | PEAK 1 | | PEAK 2 | | PEAK 3 | |
|---|---|---|---|---|---|---|
| Form. # | $T_0$ | $T_2$ | $T_0$ | $T_2$ | $T_0$ | $T_2$ |
| Commercial Enbrel ® (comparative) | 0.91 | 3.23 | 86.72 | 83.41 | 12.33 | 13.36 |
| 3:5 | 0.72 | 2.95 | 85.82 | 82.50 | 13.45 | 14.55 |
| 3:6 | 0.72 | 3.44 | 85.91 | 83.26 | 13.36 | 13.30 |
| 3:7 | 0.74 | 3.52 | 86.11 | 82.41 | 13.15 | 14.07 |
| 3:8 | 0.72 | 3.08 | 85.80 | 83.90 | 13.48 | 13.02 |
| 3:9 | 0.69 | 2.39 | 90.93 | 85.09 | 8.38 | 12.52 |
| 3:10 | 0.74 | 3.06 | 87.36 | 84.24 | 11.90 | 12.70 |
| 3:11 | 0.56 | 3.10 | 86.46 | 83.73 | 12.98 | 13.18 |
| 3:12 | 0.68 | 3.07 | 86.80 | 83.52 | 12.52 | 13.40 |
| 3:13 | 0.77 | 2.86 | 86.45 | 84.33 | 12.78 | 12.82 |
| 3:14 | 0.71 | 2.51 | 87.14 | 84.54 | 12.15 | 12.95 |

TABLE VII

HIC Data after Storage at 25° C. for 4 Weeks

| | PEAK 1 | | PEAK 2 | | PEAK 3 | |
|---|---|---|---|---|---|---|
| Form. # | $T_0$ | $T_4$ | $T_0$ | $T_4$ | $T_0$ | $T_4$ |
| Commercial Enbrel ® (comparative) | 0.91 | 1.09 | 86.76 | 86.95 | 12.33 | 11.97 |
| 3:5 | 0.54 | 1.10 | 85.12 | 84.06 | 14.33 | 14.84 |
| 3:6 | 0.55 | 1.40 | 85.50 | 84.07 | 13.96 | 14.53 |
| 3:7 | 0.74 | 1.63 | 86.11 | 85.65 | 13.15 | 12.72 |
| 3:8 | 0.72 | 1.20 | 85.80 | 85.98 | 13.48 | 12.82 |
| 3:9 | 0.69 | 1.05 | 90.93 | 86.46 | 8.38 | 12.50 |
| 3:10 | 0.74 | 1.03 | 87.36 | 85.83 | 11.90 | 13.14 |
| 3:11 | 0.56 | 1.11 | 86.46 | 85.32 | 12.98 | 13.57 |
| 3:12 | 0.68 | 0.81 | 86.80 | 86.36 | 12.52 | 12.83 |
| 3:13 | 0.77 | 1.01 | 86.45 | 85.78 | 12.78 | 13.21 |
| 3:14 | 0.71 | 1.13 | 87.14 | 85.58 | 12.15 | 13.29 |
| 4:2 | 0.63 | 1.38 | 85.16 | 84.38 | 14.21 | 14.25 |

TABLE VIII

FLOW CAM ANALYSIS OF SUBVISIBLE PARTICLES
(number of particles per ml)

| | Particle size 1-2 µm | Particle size 2-5 µm | Particle size 5-10 µm | Particle size 10-15 µm | Particle size 15-25 µm | Particle size 25-40 µm | Particle size 40-50 µm |
|---|---|---|---|---|---|---|---|
| Form 4.2 (without PS80) | 1000/ml ± 230 | 5600/ml ± 250 | 2000/ml ± 490 | 300/ml ± 71 | 91/ml ± 64 | 24/ml ± 9 | 7/ml ± 13 |
| Form 3.5 (without PS 80) | 2100 ± 1100 | 8000 ± 3900 | 2300 ± 940 | 240 ± 210 | 120 ± 84 | 60 ± 66 | 27 ± 34 |

TABLE VIII-continued

FLOW CAM ANALYSIS OF SUBVISIBLE PARTICLES
(number of particles per ml)

| | Particle size 1-2 μm | Particle size 2-5 μm | Particle size 5-10 μm | Particle size 10-15 μm | Particle size 15-25 μm | Particle size 25-40 μm | Particle size 40-50 μm |
|---|---|---|---|---|---|---|---|
| Enbrel ® | 270 ± 150 | 1400 ± 670 | 500 ± 190 | 120 ± 50 | 76 ± 41 | 27 ± 10 | 0 ± 0 |
| Form 4.2 (with PS80 | 230 ± 130 | 1200 ± 440 | 470 ± 310 | 98 ± 87 | 49 ± 57 | 16 ± 17 | 5 ± 9 |
| Form 3.5 (with PS80) | 540 ± 120 | 2600 ± 440 | 1000 ± 290 | 240 ± 81 | 44 ± 34 | 11 ± 9 | 5 ± 9 |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An aqueous pharmaceutical composition stabilized for long term storage comprising:
   etanercept at 25 to 75 mg/ml;
   a surfactant at 0.01 to 0.05% w/v;
   a metal ion selected from the group consisting of calcium, magnesium and zinc, wherein the metal ion is present at 2 mM to 20 mM;
   a buffer selected from the group consisting of phosphate, histidine, citrate, maleate, tartrate, succinate, tris-(hydroxymethyl)-aminomethane, and bicarbonate;
   wherein the composition has a pH of between 6 and 7, and the composition is free of arginine.

2. The stabilized composition of claim 1 wherein the surfactant is selected from the group consisting of polysorbate 80, polysorbate 60, polysorbate 40 and polysorbate 20.

3. The stabilized composition of claim 1 wherein the surfactant comprises polysorbate 80.

4. The stabilized composition of claim 1 wherein the composition has (i) less than 2500 particles/ml having a size of 5-10 μm; (ii) less than 3500 particles having size of about 2-5 μm and (iii) less than 700 particles/ml having size of about 1-2 μm.

5. The stabilized composition of claim 1 wherein; etanercept is present at 25 to 50 mg/ml; the metal ion is magnesium; and wherein the composition further comprises sucrose or trehalose at 0.5 to 6 wt %; NaCl at 25 to 150 mM; and the buffer is sodium phosphate at 1 to about 30 mM.

6. The stabilized composition of claim 1 wherein the metal ion is magnesium and wherein the composition further comprises NaCl at 0 to 100 mM; and the buffer is sodium phosphate at 1 to 30 mM.

7. The stabilized composition of claim 1 wherein the composition is characterized by:
   (a) an SEC analysis at $T_4$ of greater than 90 wt % monomer content; and less than 3 wt % aggregate(s) content; and
   (b) an HIC analysis at $T_2$ wherein the amount of the composition represented by peak 1 of the HIC chromatogram is less than 4 wt %; the amount of the composition represented by peak 2 of the HIC chromatogram is greater than 80 wt %; and the amount of the composition represented by peak 3 of the HIC chromatogram is less than 20 wt %; and
   (c) an HIC analysis at T4 wherein the amount of the composition represented by peak 1 of the HIC chromatogram is less than 3 wt %; the amount of the composition represented by peak 2 of the HIC chromatogram is greater than 80, wt %; and the amount of the composition represented by peak 3 of the HIC chromatogram is less than 20 wt %.

8. A vial or injection device containing the etanercept formulation of claim 1 in final dosage form.

9. A vial or injection device containing the etanercept formulation of claim 5 in final dosage form.

10. A vial or injection device containing the etanercept formulation of claim 6 in final dosage form.

11. The stabilized composition of claim 5 wherein the composition has (i) less than 2500 particles/ml having a size of 5-10 μm; (ii) less than 3500 particles having size of about 2-5 μm and (iii) less than 700 particles/ml having size of about 1-2 μm.

12. The stabilized composition of claim 6 wherein the composition has (i) less than 2500 particles/ml having a size of 5-10 μm; (ii) less than 3500 particles having size of about 2-5 μm and (iii) less than 700 particles/ml having size of about 1-2 μm.

13. The stabilized composition of claim 5 wherein the composition is characterized by:
   (a) an SEC analysis at $T_4$ of greater than 90 wt % monomer content; and less than 3 wt % aggregate(s) content; and
   (b) an HIC analysis at $T_2$ wherein the amount of the composition represented by peak 1 of the HIC chromatogram is less than 4 wt %; the amount of the composition represented by peak 2 of the HIC chromatogram is greater than 80 wt %; and the amount of the composition represented by peak 3 of the HIC chromatogram is less than 20 wt %; and
   (c) an HIC analysis at T4 wherein the amount of the composition represented by peak 1 of the HIC chromatogram is less than 3 wt %; the amount of the composition represented by peak 2 of the HIC chromatogram is greater than 80 wt %; and the amount of the composition represented by peak 3 of the HIC chromatogram is less than 20 wt %.

14. The stabilized composition of claim 6 wherein the composition is characterized by:
   (a) an SEC analysis at $T_4$ of greater than 90 wt % monomer content; and less than 3 wt % aggregate(s) content; and
   (b) an HIC analysis at $T_2$ wherein the amount of the composition represented by peak 1 of the HIC chromatogram is less than 4 wt %; the amount of the composition represented by peak 2 of the HIC chromatogram is greater than 80 wt %; and the amount of the composition represented by peak 3 of the HIC chromatogram is less than 20 wt %; and
   (c) an HIC analysis at T4 wherein the amount of the composition represented by peak 1 of the HIC chromatogram is less than 3 wt %; the amount of the composition represented by peak 2 of the HIC chromatogram is greater than 80 wt %; and the amount of the composition represented by peak 3 of the HIC chromatogram is less than 20 wt %.

15. The stabilized composition of claim 1, wherein a number of sub-visible particles per ml of the formulation having size of 1-10 μm is at least about 50% lower than in the same composition having no surfactant.

16. The composition of claim 1, wherein said composition has less than about 1 wt % aggregate(s) content as determined by size exclusion chromatography after 4 weeks storage at 25° C.

17. An aqueous pharmaceutical composition comprising:
etanercept at about 50 mg/ml;
up to 0.05% w/v surfactant;
2 mM to 20 mM metal ion;
about 25 mM to about 100 mM NaCl;
10 mM to 200 mM of a phosphate or citrate buffer;
  wherein the composition has a pH of between 6 and 7,
  wherein the composition is free of arginine,
  wherein said composition has less than about 1 wt % aggregate(s) content as determined by size exclusion chromatography after 4 weeks storage at 25° C., and
  wherein the formulation has:
  (i) less than about 2500 particles/ml having a size of about 5-10 μm;
  (ii) less than about 3500 particles having size of about 2-5 μm, and
  (iii) less than about 700 particles/ml having size of about 1-2 μm.

\* \* \* \* \*